(12) United States Patent
Medof et al.

(10) Patent No.: US 10,933,093 B2
(45) Date of Patent: *Mar. 2, 2021

(54) COMPOSITIONS AND METHODS OF TREATING A T CELL MEDIATED DISORDER

(71) Applicant: CASE WESTERN RESERVE UNIVERSITY, Cleveland, OH (US)

(72) Inventors: M. Edward Medof, Cleveland, OH (US); Feng Lin, Cleveland, OH (US); Michael G. Strainic, Cleveland, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/950,038

(22) Filed: Apr. 10, 2018

(65) Prior Publication Data
US 2018/0228843 A1    Aug. 16, 2018

Related U.S. Application Data

(63) Continuation of application No. 15/077,256, filed on Mar. 22, 2016, now Pat. No. 9,937,206, which is a continuation of application No. 13/505,976, filed as application No. PCT/US2010/055445 on Nov. 4, 2010, now Pat. No. 9,290,736.

(60) Provisional application No. 61/258,058, filed on Nov. 4, 2009.

(51) Int. Cl.
| | |
|---|---|
| *C12N 5/071* | (2010.01) |
| *C12N 5/00* | (2006.01) |
| *C12N 5/02* | (2006.01) |
| *A61K 35/17* | (2015.01) |
| *C12N 5/0783* | (2010.01) |
| *A61K 38/00* | (2006.01) |
| *A61K 35/12* | (2015.01) |

(52) U.S. Cl.
CPC ............ *A61K 35/17* (2013.01); *C12N 5/0636* (2013.01); *A61K 38/00* (2013.01); *A61K 2035/122* (2013.01); *A61K 2035/124* (2013.01); *C12N 2501/998* (2013.01)

(58) Field of Classification Search
None
See application file for complete search history.

(56) References Cited

U.S. PATENT DOCUMENTS

| | | |
|---|---|---|
| 2006/0062763 A1 | 3/2006 | Godfrey et al. |
| 2011/0300119 A1 | 12/2011 | Tran et al. |
| 2014/0348808 A1 | 11/2014 | De La Rosa |

FOREIGN PATENT DOCUMENTS

| | | |
|---|---|---|
| WO | 2009/111701 A2 | 9/2009 |

OTHER PUBLICATIONS

Strainic et al., "C5a-05aR and C3a-C3aR interactions control whether T cells generate Th1 or Th2 cytokines", 2007, Mol. Immunol. vol. 44: 244.
Chevalier et al., "The split personality of regulatory T cells in HIV infection", 2013, Blood. vol. 121: 29-37.
Mor et al., "Identification of Aldolase as a Target Antigen in Alzheimer's Disease", 2005, J. Immunol. vol. 175: 3439-45.
Shi et al., "CD4+Foxp+regulatory T cells induced by RGF-B and all-trans retinoic acid attenuate obliterative bronchiolitis in rat trachea transplantation", 2011, Int. Immunopharm. vol. 11: 1887-94.
Liszewski et al., "Intracellular Complement Activation Sustains T Cell Homeostasis and Mediates Effector Differentiation", 2013, Immunity, vol. 39: 1143-1157.
Janeway et al., "The complement System and Innate Immunity", 2001, 1-15.
Chen et al., "TGF-B and Adaptive Foxp3+ Regulatory T cells", 2010, J. Mol. Cell. Biol. vol. 2: 30-36.
Mathieu et al. "The C3a receptor antagonist SB 290157 has agonist activity", Immunology Letters 100 (2005) 139-145.
Wang et al., "Anti-C5 monoclonal antibody therapy prevents collagen-induced arthritis and ameliorates established disease", Proc. Natl. Acad. Sci., vol. 92, pp. 8955-8959, Sep. 1995.

*Primary Examiner* — Amy E Juedes
(74) *Attorney, Agent, or Firm* — Tarolli, Sundheim, Covell & Tummino LLP

(57) ABSTRACT

A method of generating a CD4$^+$FoxP3$^+$ Treg cell, the method includes administering at least one complement antagonist to a naive CD4$^+$ T cell at an amount effective to substantially inhibits C3a receptor (C3aR) and/or C5a receptor (C5aR) signal transduction in the CD4$^+$ T cell, induce TGF-β1 expression of the CD4$^+$ T cell, and induce differentiation of the of the naive CD4$^+$ T cell into a CD4$^+$FoxP3$^+$ Treg cell.

9 Claims, 5 Drawing Sheets

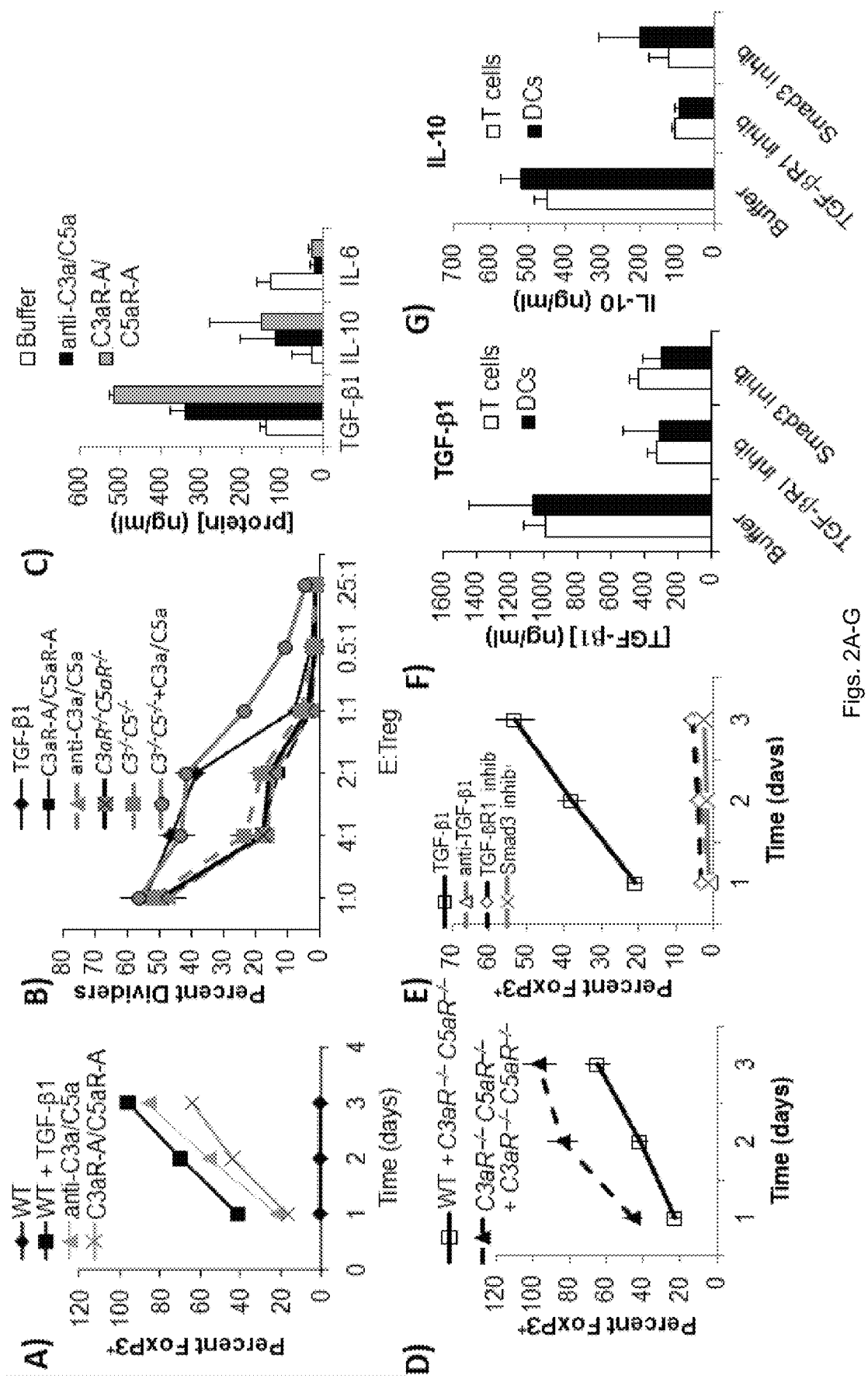
Figs. 2A-G

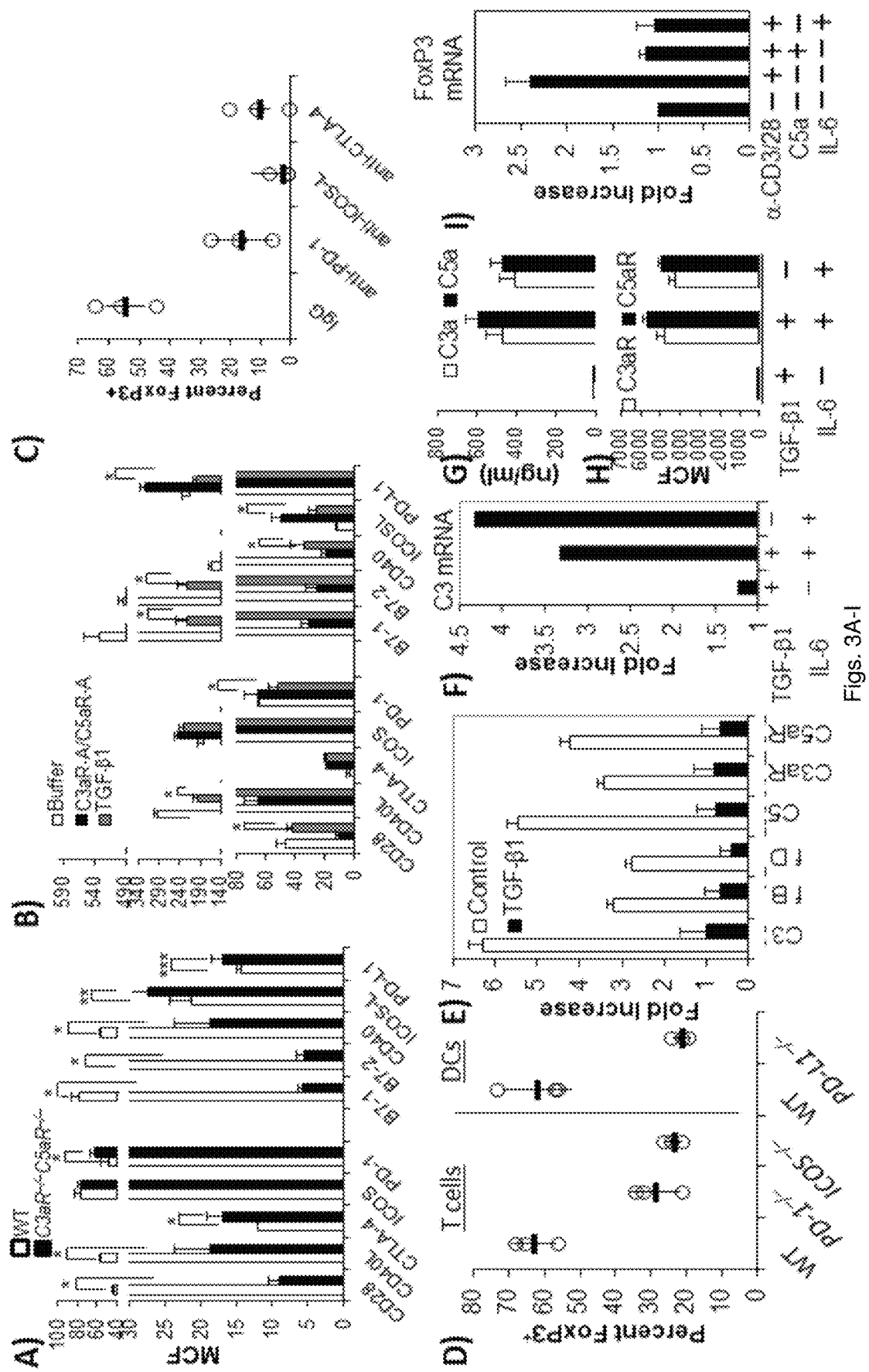
Figs. 3A-I

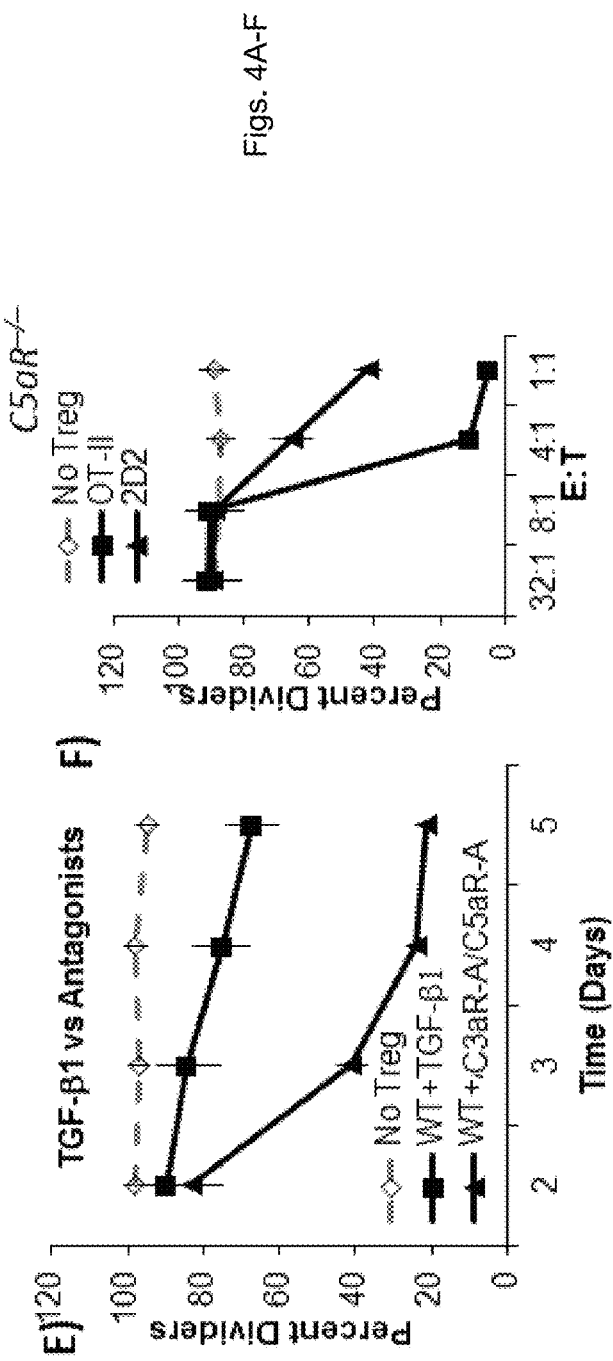
Figs. 4A-F

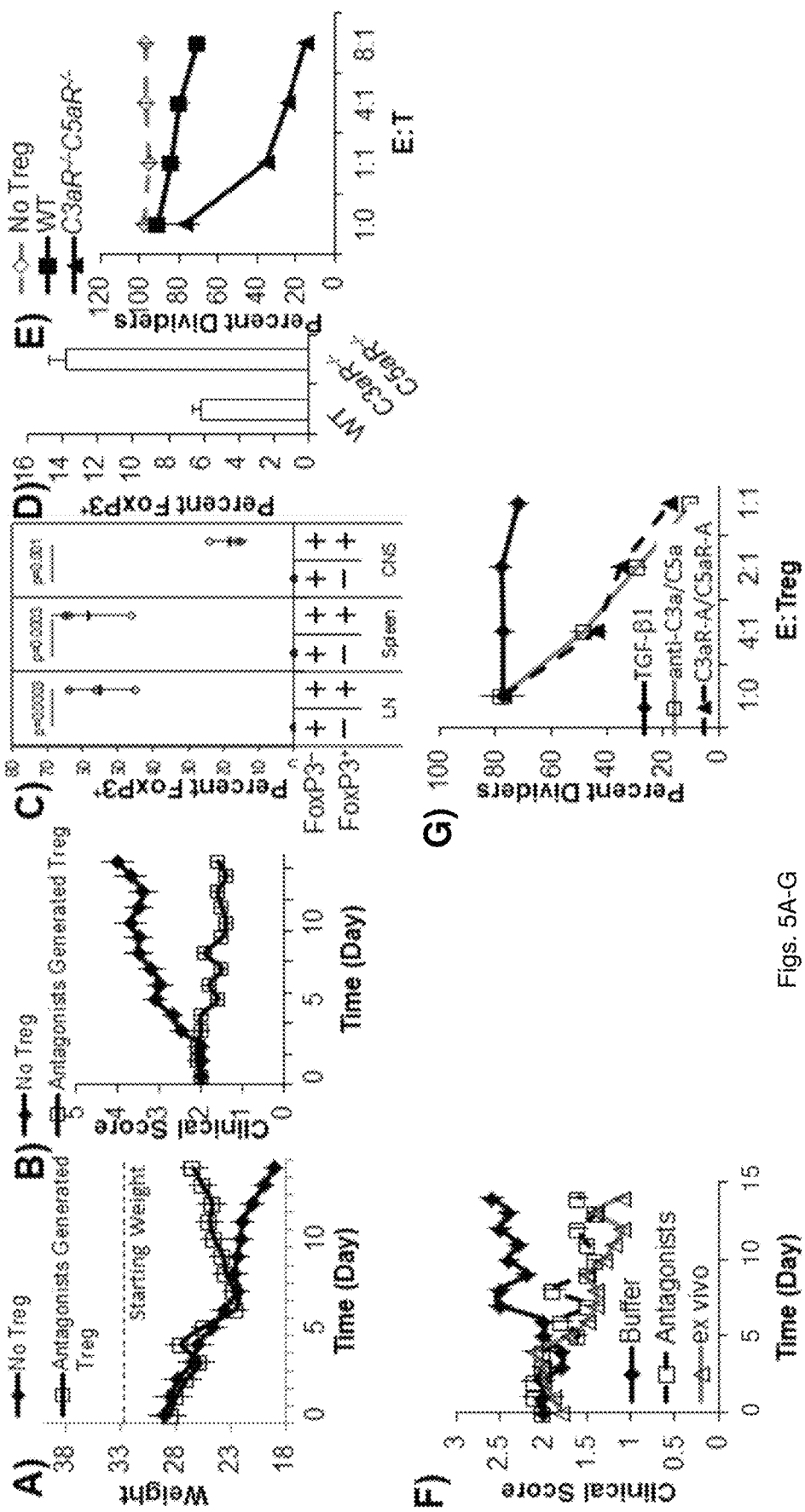
Figs. 5A-G

COMPOSITIONS AND METHODS OF TREATING A T CELL MEDIATED DISORDER

RELATED APPLICATION

This application is a Continuation of U.S. patent application Ser. No. 15/077,256, filed Mar. 22, 2016, now U.S. Pat. No. 9,937,206, which is a Continuation of U.S. patent application Ser. No. 13/505,976, filed May 3, 2012, now U.S. Pat. No. 9,290,736, which is a 371 of PCT/US2010/055445, filed Nov. 4, 2010, which claims priority from U.S. Provisional Application No. 61/258,058, filed Nov. 4, 2009, the subject matter, which is incorporated herein by reference.

GOVERNMENT FUNDING

This invention was made with government support under Grant No. NS052471 and AI023598 awarded by The National Institutes of Health. The United States Government has certain rights in the invention.

TECHNICAL FIELD

The present application generally relates to methods for generating FoxP3+ cells and also to methods of treating a T cell mediated disorder.

BACKGROUND

T cell responses must adequately defend against pathogens but should terminate once they have eliminated the pathogen that elicited them. In the absence of this control, lymphoproliferation would continue unabated and antithetically would destroy the host. T cell responses are regulated by dendritic cells (DCs) which are educated by the local factors they sense. It is widely accepted that toll like receptor (TLR) signaling triggered by pathogen components educates them to initiate T effector cell responses. This process, in large part, involves upregulation of their MHC class II and B7/CD40 costimulatory molecule expression. The absence of TLR signals in conjunction with locally produced immunosuppressive cytokines educates DCs to extinguish T cell responses by producing T regulatory (Treg) cells. Central among these cells are antigen specific (induced) FoxP3+ Treg cells. In conjunction with nuclear expression of the forkhead/winged-helix family transcription factor (TF) member, FoxP3, these cells surface express CD25, the a chain of the IL-2 receptor (IL-2R) which greatly augments its affinity for IL-2, and CTLA-4, a potent inhibitor of B7 induced CD28 signaling in T effectors needed both for their proliferation and their survival.

SUMMARY

This application relates generally to a method of generating CD4+FoxP3+ Treg cells using complement antagonists, and also to therapeutic methods of treating T cell mediated disorders in a subject. According to one aspect of the application, a method is provided for generating CD4+ FoxP3+ Treg cells. The method includes administering at least one complement antagonist to a naive CD4+ T cell at an amount effective to substantially inhibit C3a receptor (C3aR) and/or C5a receptor (C5aR) signal transduction in the CD4+ T cell, induce TGF-β expression of the CD4+ T cell, and induce differentiation of the of the naive CD4+ T cell into a CD4+FoxP3+ Treg cell.

In an aspect of the application, the at least one complement antagonist is selected from the group consisting of a small molecule, a polypeptide, and a polynucleotide. In some aspects, the polypeptide includes an antibody directed against at least one of C3, C5, C3 convertase, C5 convertase, C3a, C5a, C3aR, or C5aR. In other aspects, the polypeptide can include decay accelerating factor (DAF) (CD55) that accelerates the decay of C5 convertase and C3 convertase. In some aspects, the polynucleotide includes a small interfering RNA directed against a polynucleotide encoding at least one of C3, C5, C3aR, or C5aR.

Another aspect of the application relates to a method of treating a T cell mediated disorder in a subject. The method includes administering at least one complement antagonist to a naive CD4+ T cell at an amount effective to substantially inhibits C3a receptor (C3aR) and/or C5a receptor (C5aR) signal transduction in the CD4+ T cell, induce TGF-β expression of the CD4+ T cell, and induce differentiation of the of the naive CD4+ T cell into a CD4+ FoxP3+ Treg cell. A therapeutically effective amount of the CD4+ FoxP3+ Treg cells is then administered to the subject to treat the T cell mediated disorder.

In some aspects of the present application, the T cell mediated disorder is selected from the group consisting of achlorhydra autoimmune active chronic hepatitis, acute disseminated encephalomyelitis, acute hemorrhagic leukoencephalitis, Addison's disease, agammaglobulinemia, alopecia areata, Alzheimer's disease, amyotrophic lateral sclerosis, ankylosing spondylitis, anti-gbm/tbm nephritis, antiphospholipid syndrome, antisynthetase syndrome, aplastic anemia, arthritis, atopic allergy, atopic dermatitis, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune polyendocrine syndrome, autoimmune progesterone dermatitis, autoimmune thrombocytopenia purpura, autoimmune uveitis, balo disease/balo concentric sclerosis, Bechets syndrome, Berger's disease, Bickerstaff's encephalitis, Blau syndrome, bullous pemphigoid, Castleman's disease, Chagas disease, chronic fatigue immune dysfunction syndrome, chronic inflammatory demyelinating polyneuropathy, chronic lyme disease, chronic obstructive pulmonary disease, Churg-Strauss syndrome, cicatricial pemphigoid, coeliac disease, Cogan syndrome, cold agglutinin disease, cranial arteritis, crest syndrome, Crohns disease, Cushing's syndrome, Dego's disease, Dercum's disease, dermatitis herpetiformis, dermatomyositis, diabetes mellitus type 1, Dressler's syndrome, discoid lupus erythematosus, eczema, endometriosis, enthesitis-related arthritis, eosinophilic fasciitis, epidermolysis bullosa acquisita, essential mixed cryoglobulinemia, Evan's syndrome, fibrodysplasia ossificans progressive, fibromyalgia, fibromyositis, fibrosing aveolitis, gastritis, gastrointestinal pemphigoid, giant cell arteritis, glomerulonephritis, Goodpasture's syndrome, Graves' disease, Guillain-barré syndrome (GBS), Hashimoto's encephalitis, Hashimoto's thyroiditis, henoch-schonlein purpura, hidradenitis suppurativa, Hughes syndrome, inflammatory bowel disease (IBD), idiopathic inflammatory demyelinating diseases, idiopathic pulmonary fibrosis, idiopathic thrombocytopenic purpura, iga nephropathy, inflammatory demyelinating polyneuopathy, interstitial cystitis, irritable bowel syndrome (IBS), Kawasaki's disease, lichen planus, Lou Gehrig's disease, lupoid hepatitis, lupus erythematosus, ménière's disease, microscopic polyangiitis, mixed connective tissue disease, morphea, multiple myeloma, multiple sclerosis, myasthenia gravis, myositis, narcolepsy, neuromyelitis optica, neuromyotonia, occular cicatricial pemphigoid, opsoclonus myoclonus syndrome, ord thyroiditis, Parkinson's disease, pars planitis, pemphigus, pemphigus vulgaris, pernicious anaemia, polymyalgia rheumatic, polymyositis, primary biliary cirrhosis, primary sclerosing cholangitis, progressive inflammatory neuropathy, psoriasis, psoriatic arthritis, raynaud phenomenon, relapsing polychondritis, Reiter's syndrome, rheumatoid arthritis, rheumatoid fever, sarcoidosis, schizophrenia, Schmidt syndrome, Schnitzler syndrome, scleritis, scleroderma, Sjögren's syndrome, spondyloarthropathy, sticky blood syndrome, still's disease, stiff person syndrome, sydenham chorea, sweet syndrome, takayasu's arteritis, temporal arteritis, transverse myelitis, ulcerative colitis, undifferentiated connective tissue disease, undifferentiated spondyloarthropathy, vasculitis, vitiligo, Wegener's granulomatosis, Wilson's syndrome, Wiskott-Aldrich syndrome, hypersensitivity reactions of the skin, atherosclerosis, ischemia-reperfusion injury, myocardial infarction, and restenosis.

A further aspect of the application relates to a method of treating inflammation in a subject. The method includes administering at least one complement antagonist to a naive CD4$^+$ T cell at an amount effective to substantially inhibits C3a receptor (C3aR) and/or C5a receptor (C5aR) signal transduction in the CD4$^+$ T cell, induce TGF-β expression of the CD4$^+$ T cell, and induce differentiation of the of the naive CD4$^+$ T cell into a CD4$^+$FoxP3$^+$ Treg cell. A therapeutically effective amount of the CD4$^+$FoxP3$^+$ Treg cells is then administered to the subject to treat the inflammation.

Yet another aspect of the application relates to a method of treating a T cell mediated disease in a subject. The method includes administering to the subject a therapeutically effective amount of at least one complement antagonist and a pharmaceutically acceptable carrier. The at least one complement antagonist can substantially inhibit interaction of at least one of C3a or C5a with the C3a receptor (C3aR) and C5a receptor (C5aR) on interacting dendritic cells and CD4$^+$ T cells in the subject. The at least one complement antagonist advantageously does not substantially inhibit innate systemic complement activation in the subject.

BRIEF DESCRIPTION OF THE DRAWINGS

The foregoing and other features of the application will become apparent to those skilled in the art to which the application relates upon reading the following description with reference to the accompanying drawings, in which:

FIGS. 2(A-G) illustrate plots and graphs showing: A) $1\times10^6$ CD62L$^{hi}$CD25$^-$ CD4$^+$ cells from FoxP3-GFP knockin mice were incubated with anti-CD3, 5 ng/ml rhIL-2, and $1\times10^5$ CD11c$^+$ WT DCs for 3 days together with 5 ng/ml rhTGF-β1 (Prospecbio), 10 nM C3aR-A/C5aR-A, or 5 μg/ml anti-C3a/C5a mAbs and assayed for CD25 and FoxP3 expression by flow cytometry. B) Sorted $1\times10^6$ FoxP3$^+$ cells were incubated with increasing amounts of CellTracker Red labeled CD25$^-$CD4$^+$ WT cells and 2 μg/ml anti-CD3+$1\times10^5$ CD11c$^+$ DCs for 4 days and percent dividers determined. C) $1\times10^6$ CD62L$^{hi}$CD25$^-$ CD4$^+$ cells from FoxP3-GFP knockin mice were incubated as in (A) and assayed for IL-6, TGF-β1, and IL-10 expression by ELISA. D) $1\times10^6$ CD62L$^{hi}$CD25$^-$ CD4$^+$ cells from WT or C3aR$^{-/-}$C5aR$^{-/-}$ mice were incubated with CD11c$^+$ DCs from C3aR$^{-/-}$C5aR$^{-/-}$ mice and 5 ng/ml rhIL-2 for 3 days after which cells were assayed for FoxP3 expression by flow cytometry. E-G) CD4$^+$CD25$^-$ cells from WT or C3aR$^{-/-}$C5aR$^{-/-}$ mice were incubated with anti-CD3 mAb, IL-2, and DCs±anti-TGF-β mAb, TGF-βR1 inhibitor or Smad3 inhibitor for 3 days and E) assessed FoxP3$^+$ Treg numbers by flow cytometry, and assayed culture supernatants of CD4$^+$ cells and DCs for F) TGF-β1 and G) IL-10.

FIGS. 3(A-I) illustrate graphs showing: A) $1\times10^6$ CD62L$^{hi}$CD25$^-$CD4$^+$ cells from WT or C3aR$^{-/-}$C5aR$^{-/-}$ mice were incubated with anti-CD3/CD28 Dynabead activation beads, 5 ng/ml rhIL-2, and $1\times10^5$ CD11c$^+$ WT DCs for 3 days. The CD4$^+$ cell and DC partners were sorted, after which the DCs were assayed for B7 family members (*P<0.01; P<0.03; *P=0.07) and the CD4$^+$ cells were assayed for B7 coinhibitory counter-receptors by flow. B) $1\times10^6$ CD62L$^{hi}$CD25$^-$CD4$^+$ cells from WT mice were incubated with anti-CD3/CD28 Dynabead activation beads, 5 ng/ml rhIL-2, and $1\times10^5$ CD11c$^+$ WT DCs for 3 days±10 nM C3aR-A/C5aR-A or ±5 ng/ml rhTGF-fβ1. The CD4$^+$ cell and DC partners were sorted, after which the cells were assayed as in (A; *P<0.01 C3aR-A/C5aR-A vs. TGF-β1). C) $1\times10^6$ CD62L$^{hi}$CD25$^-$ CD4$^+$ cells from WT or C3aR$^{-/-}$C5aR$^{-/-}$ were incubated with anti-CD3/CD28 Dynabead activation beads, 5 ng/ml rhIL-2, and $1\times10^5$ CD11c$^+$ WT DCs for 3 days in the presence of blocking anti-CTLA-4, anti-PD-1, or anti-ICOS-L Abs and percent FoxP3$^+$ cells assayed by flow cytometry. D) $1\times10^6$ CD62L$^{hi}$CD25$^-$ CD4$^+$ cells from WT, ICOS$^{-/-}$, or PD-1$^{-/-}$ were incubated with anti-CD3/CD28 Dynabead activation beads, 5 ng/ml rhIL-2, and $1\times10^3$ CD11c$^+$ WT or PD-L1$^{-/-}$ DCs for 3 days in the presence of blocking anti-CTLA-4, anti-PD-1, or anti-ICOS-L Abs and percent FoxP3$^+$ cells assayed by flow cytometry. E) Anti-CD3/CD28 stimulated CD4$^+$ cells were treated with TGF-β1 or buffer and complement mRNA transcripts were assayed by qPCR. F-H) $1\times10^4$ CD62L$^{hi}$CD25$^-$ CD4$^+$ cells from C57BL/6 mice were incubated with anti-CD3/CD28 Dynabeads and 5 ng/ml rhIL-2 for 3 days in the presence of TGF-β, TGF-β+IL-6, or IL-6 after which cells were assayed for (F) C3 mRNA expression by qPCR, (G) C3 and C5a generation by ELSIA, and (H) C3aR and C5aR surface expression by flow cytometry. I) C57BL/6 CD4$^+$ T cells were incubated for 1 hr with anti-CD3/CD28±100 ng/ml C5a and FoxP3 mRNA was quantitated by qPCR.

FIGS. 4(A-F) illustrate plots and graphs showing: A-B) CFSE-labeled OT-II cells were adoptively transferred into WT mice. Two days later CD4$^+$CD25$^-$ Daf1$^{-/-}$ and C3aR$^{-/-}$C5aR$^{-/-}$ cells from OT-II mice were adoptively transferred and the mice were immunized with ovalbumin in CFA. A) Percent CD25$^+$ cells in draining LN were assessed by flow cytometry, and (B) CFSE dilution was assessed 5 days later. CD) CellTracker Red-labeled OT-II cells were adoptively transferred into WT or C3aR$^{-/-}$ C5aR$^{-/-}$ mice. Two days later CD4$^+$CD25$^-$ cells from FoxP3-GFP OT-II mice were adoptively transferred and the mice were immunized with ovalbumin in CFA. C) Percent FoxP3$^+$ cells in draining LN were assessed by flow cytometry, and (D) CellTracker Red dilution was assessed 5 days later. E) $10^6$ CellTracker Red labeled OT-II cells were transferred into WT mice. Two days later, Tregs generated from naive CD4$^+$ cells of FoxP3-GFP mice in vitro by incubation with TGF-β1 or 10 nM C3aR/C5aR antagonists were adoptively transferred into WT recipients and the mice were immunized with ovalbumin in CFA. CellTracker Red dilution in the OT-II cells in the spleen assessed 5 days thereafter. F) Tregs were generated from naive CD4⁺ OT-II or 2D2 cells (MOG$_{35-55}$ specific) in vitro as in (E) using 10 nM C3aR-A/C5aR-A. $10^6$ Cell-Tracker Red labeled OT-II cells were co-transferred into WT mice in 32:1, 8:1, 4:1, and 1:1 E:T ratios with 1) the OT-II Tregs labeled with CellTracker Violet, 2) the 2D2 Tregs labeled with CFSE, or 3) a 50/50 mixture of both. Two days thereafter, mice were immunized with ovalbumin in CFA and 5 days later percent CellTracker Red dividers was determined by flow cytometry.

FIGS. 5(A-G) illustrate graphs showing, A-C) EAE was induced in FoxP3-GFP knockin mice and 10 days after disease onset, CD4 cells were isolated from spleens and lymph nodes and sorted on GFP. $4\times10^6$ GFP negative cells were adoptively transferred into Rag2$^{-/-}$ mice. The mice were subsequently injected with $1\times10^6$ FoxP3-GFP positive cells or PBS after which A) weight change, B) clinical scores, and C) percent FoxP3⁺ cells were assayed. D-E) EAE was induced in WT and C3aR$^{-/-}$C5aR$^{-/-}$ mice and at day 12 post disease induction draining LN cells were harvested and assayed for D) % FoxP3⁺ cells, and E) suppressive capacity as above. F) EAE was induced in FoxP3-GFP knockin mice and 10 days after induction mice were treated with buffer control, C3aR-A/C5aR-A, or ex vivo generated FoxP3⁺ Tregs (from FoxP3-GFP mice with C3aR-A/C5aR-A), after which C) clinical scores were assessed. G) CD25⁺ cells from $1\times10^6$ CD25⁻CD4⁺ Human T cells isolated by flow cytometry and incubated with soluble anti-CD3, IL-2, and autologous DCs in the presence and absence of TGF-β, C3aR-A/C5aR-A, or anti-C3a/C5a mAbs for 3 days were incubated with CFSE labeled autologous naive T cells, anti-CD3, and autologous DCs and percent dividers determined 3 days thereafter by CFSE dilution.

DETAILED DESCRIPTION

Figure 1:
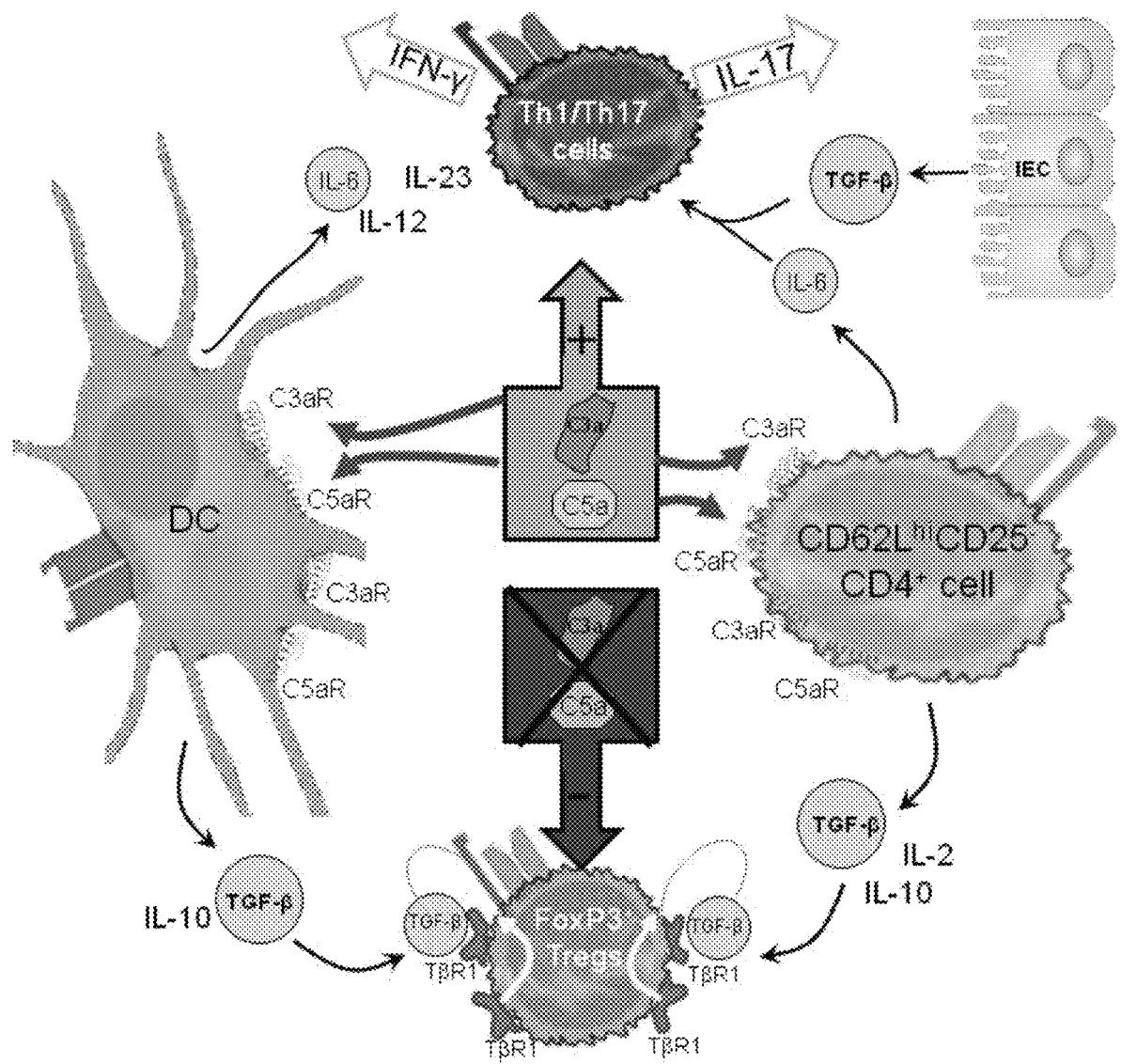
FIG. 1 illustrates a schematic drawing of dendritic cell (DC)-CD4$^+$ cell C3aR/C5aR signal transduction driving Th1/Th7 responses and the absence of these signals driving FoxP3$^+$ Treg induction and TGF-β/IL-10 expression.

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present application pertains. Commonly understood definitions of molecular biology terms can be found in, for example, Rieger et al., *Glossary of Genetics: Classical and Molecular*, 5th Edition, Springer-Verlag: New York, 1991, and Lewin, *Genes V*, Oxford University Press: New York, 1994. The definitions provided herein are to facilitate understanding of certain terms used frequently herein and are not meant to limit the scope of the present application.

In the context of the present application, the term "polypeptide" refers to an oligopeptide, peptide, or protein sequence, or to a fragment, portion, or subunit of any of these, and to naturally occurring or synthetic molecules. The term "polypeptide" also includes amino acids joined to each other by peptide bonds or modified peptide bonds, i.e., peptide isosteres, and may contain any type of modified amino acids. The term "polypeptide" also includes peptides and polypeptide fragments, motifs and the like, glycosylated polypeptides, and all "mimetic" and "peptidomimetic" polypeptide forms.

As used herein, the term "polynucleotide" refers to oligonucleotides, nucleotides, or to a fragment of any of these, to DNA or RNA (e.g., mRNA, rRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, siRNAs, microRNAs, and ribonucleoproteins. The term also encompasses nucleic acids, i.e., oligonucleotides, containing known analogues of natural nucleotides, as well as nucleic acid-like structures with synthetic backbones.

As used herein, the term "antibody" refers to whole antibodies, e.g., of any isotype (IgG, IgA, IgM, IgE, etc.), and includes fragments thereof which are also specifically reactive with a target polypeptide. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain polypeptide. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term "antibody" also includes polyclonal, monoclonal, or other purified preparations of antibodies, recombinant antibodies, monovalent antibodies, and multivalent antibodies. Antibodies may be humanized, and may further include engineered complexes that comprise antibody-derived binding sites, such as diabodies and triabodies.

As used herein, the term "complementary" refers to the capacity for precise pairing between two nucleobases of a polynucleotide and its corresponding target molecule. For example, if a nucleobase at a particular position of a polynucleotide is capable of hydrogen bonding with a nucleobase at a particular position of a target polynucleotide (the target nucleic acid being a DNA or RNA molecule, for example), then the position of hydrogen bonding between the polynucleotide and the target polynucleotide is considered to be complementary. A polynucleotide and a target polynucleotide are complementary to each other when a sufficient number of complementary positions in each molecule are occupied by nucleobases, which can hydrogen bond with each other. Thus, "specifically hybridizable" and "complementary" are terms which can be used to indicate a sufficient degree of precise pairing or complementarity over a sufficient number of nucleobases such that stable and specific binding occurs between a polynucleotide and a target polynucleotide.

As used herein, the terms "effective," "effective amount," and "therapeutically effective amount" refer to that amount of a complement antagonist and/or a pharmaceutical composition thereof that results in amelioration of symptoms or a prolongation of survival in a subject with a T cell mediated disease or related disorder. A therapeutically relevant effect relieves to some extent one or more symptoms of a T cell mediated disease related disorder, or returns to normal either partially or completely one or more physiological or biochemical parameters associated with or causative of a T cell mediated disease or related disorder.

As used herein, the term "subject" refers to any warm-blooded organism including, but not limited to, human beings, rats, mice, dogs, goats, sheep, horses, monkeys, apes, rabbits, cattle, etc.

As used herein, the terms "complement polypeptide" or "complement component" refer to a polypeptide (or a polynucleotide encoding the polypeptide) of the complement system that functions in the host defense against infections and in the inflammatory process. Complement polypeptides constitute target substrates for the complement antagonists provided herein.

As used herein, the term "complement antagonist" refers to a polypeptide, polynucleotide, or small molecule capable of substantially reducing expression of C3, C5, C3a, C5a, C5aR, and/or C3aR in CD4+ T cells or dendritic cells (DCs), substantially inhibiting C3aR and/or C5aR signal transduction of CD4+ T cells, and/or substantially reducing interaction of C3a and C5a with C3aR and C5aR expressed by interacting dendritic cells (DCs) and CD4+ T cells.

This application generally relates to a method of generating CD4+FoxP3+ Treg cells using complement antagonists and also to therapeutic preparations for the treatment of a T cell mediated disorder or condition. It was found that during wild type dendritic cell (WT DC)-CD4+ T cell interactions, both cells locally synthesize the alternative complement pathway (AP) components C3, factor B, factor D, in conjunction with C5, C3aR and C5aR, the latter receptors being G protein coupled receptors (GPCRs). Concurrently with this, both cells downregulate their surface expression levels of DAF. As a result of DAF inhibition, C3/C5 convertase assemble at the adjoining DC-CD4+ cell surfaces and act on the locally synthesized C3/C5 to generate C3a/C5a. Bidirectional interaction of these cytokine-like fragments with upregulated C3aR/C5aR on the interacting DCs and CD4+ cells then transduces GPCR signals, which are needed both for CD4+ cell IL-2 production and DC innate cytokine production, which evokes CD4+ cell differentiation into Th1/Th17 effectors (FIG. 1). The underlying mechanism is that upon C3aR/C5aR activation by ligation of locally produced C3a and C5a, PI-3 kinase γ (PI-3Kγ) activity is upregulated leading to increased intracellular AKT phosphorylation and downstream signaling to NF-kB. Consistent with this, we found that C3aR/C5aR signals are required for T cell survival not only during activation but also tonically in the spleen. The immunological significance of these GPCR signals is that they 1) upregulate DC MHC class II and DC-T cell costimulatory molecule expression and 2) concurrently sustain intracellular Bcl-2/Bcl-x2 expression and suppress surface Fas/FasL expression in T cells.

It was found that when autocrine/paracrine C3aR/C5aR signaling between interacting dendritic cells (DCs) and naive CD4+ cells (devoid of FoxP3+ cells) does not occur, TGF-β is endogenously produced by both cell partners. In both primed DCs and naive CD4+ cells, the elicited TGF-β enters into autocrine signaling loops that suppresses costimulatory molecule expression and IL-6 production. Auto-inductive TGF-β signaling prevents upregulation of costimulatory CD28 and CD40 ligand (CD40L) expression and thereby allows FoxP3+ Treg induction.

As shown in the Example, C3aR and/or C5aR signaling of naive CD4+ cells can be substantially inhibited and FoxP3+ Tregs can be induced from the CD4+ cells by administering to the CD4+ cells a pharmaceutical composition comprising C3aR and/or C5aR antagonists (C3aR-A and/or C5aR-A) and/or anti-C3a and/or anti-C5a monoclonal antibodies. Human induced FoxP3+ (iFoxP3+) Tregs produced in this way exert robust suppressive activity when added to DC, anti-CD3 and CFSE-labeled CD25− CD4+ cell mixtures from the same individual and confer about 4 about 10 fold greater suppression than FoxP3+ Tregs generated by exogenously adding TGF-β CD4+ cells. This shows that complement antagonists, such as C3, C5, C3C5aR, C3aR, C5a, or C3a antagonists (e.g., competitive inhibitors, mAbs, interfering RNA) as well as DAF, used alone, or in combination, that inhibit C3aR and/or C5aR signaling in the CD4+ T cell will not only promote or induce the generation of FoxP3+ Treg cells, but when administered to a subject can be used to treat a T cell mediated diseases and disorders in a subject.

One aspect of the application, therefore, relates to a method of generating CD4+FoxP3+ Treg cells by administering at least one complement antagonist to a naive CD4+ T cell at an amount effective to substantially inhibit C3a receptor (C3aR) and/or C5a receptor (C5aR) signal transduction in the CD4+ T cell, induce TGF-β expression of the CD4+ T cell, and induce differentiation of the of the naive CD4+ T cell into a CD4+FoxP3+ Treg cell.

In some aspects of the application, the complement antagonist can substantially inhibit the interaction of at least one of C3a or C5a with the C3a receptor (C3aR) and C5a receptor (C5aR) on the CD4+ T cells to substantially inhibit C3a receptor (C3aR) and/or C5a receptor (C5aR) signal transduction in the CD4+ T cell. Disabling these interactions results in the induction of CD4+FoxP3+ Treg cells. In other aspects of the application, an inhibition or reduction in the functioning of a C3/C5 convertase can prevent cleavage of C5 and C3 into C5a and C3a, respectively. An inhibition or reduction in the functioning of C5a and C3a polypeptides can reduce or eliminate the ability of C5a and C3a to interact with C5aR and C3aR of CD4+ cells and substantially inhibit C3a receptor (C3aR) and/or C5a receptor (C5aR) signal transduction in the CD4+ T cell. An inhibition or reduction in the functioning of a C5aR or C3aR may similarly reduce or eliminate the ability of C5a and C3a to interact C5aR and C3aR, respectively, and substantially inhibit C3a receptor (C3aR) and/or C5a receptor (C5aR) signal transduction in the CD4+ T cell.

In other aspects of the application, the at least one complement antagonist can substantially induces naive CD4+ cell expression of CD25, CTLA-4, FoxP3, DAF and C5L2, downregulates dendritic cell B7/CD40 and CD4+ effector cell CD28/CD40 ligand costimulatory molecule expression, and inhibits dendritic cell C5a/C3a production and CD4+ cell C5aR/C3aR signal transduction in the subject.

In some embodiments of the application, the complement antagonist can include at least one of a C5a antagonist, a C3a antagonist, a CSaR antagonist, or a C3aR antagonist. FoxP3+ cells can be generated by blocking C3a or C5a. C3a and C5a can be blocked during cognate APC-T cell interactions using mAbs directed toward C5a and C3a. It is also contemplated that more than one complement antagonist can be administered concurrently to naive CD4+ T cells in the presence of cognate dendritic cells in order to inhibit C3a/C5a production and/or DC-T cell C3aR/C5aR signal transduction.

In some embodiments, the at least one complement antagonist can include various C5aR antagonists known in the art. For example, C5aR antagonists include those described by Short et al. (1999) *Effects of a new C5a receptor antagonist on C5a-and endotoxin-induced neutropenia in the rat*. British Journal of Pharmacology, 125:551-554, Woodruff et al. (2003) *A Potent C5a Receptor Antagonist Protects against Disease Pathology in a Rat Model of Inflammatory Bowel Disease*. The Journal of Immunology, 171:5514-5520, Sumichika et al. (2002) *Identification of a Potent and Orally Active Non-peptide C5a Receptor Antagonist*. The Journal of Biological Chemistry, 277(51): 49403-49407, all of which are incorporated herein by reference.

In one embodiment, CSaRantagonist can include the peptidomimetic C5aR antagonist JPE-1375 (Jerini AG, Germany). C5aR antagonists can further include small molecules, such as CCX168 (ChemoCentryx, Mountain View, Calif.).

In other embodiments, the at least one complement antagonist can include an antibody or antibody fragment directed against a complement component that can affect or inhibit the formation of C3a and/or C5a (e.g., DAF, anti-C5 convertase, and anti-C3 convertase) and/or reduce C5a/C3a-C5aR/C3aR interactions (e.g., anti-C5a, anti-C3a, anti-C5aR, C3aR antibodies).

In still other embodiments, the at least one complement antagonist can include an antibody or antibody fragment directed against a complement component that can affect or inhibit the formation of C3a and/or C5a (e.g., anti-Factor B, anti-Factor D, anti-C5, anti-C3, ant-C5 convertase, and anti-C3 convertase) and/or reduce C5a/C3a-C5aR/C3aR interactions (e.g., anti-05a, anti-C3a, anti-05aR, and C3aR antibodies). In one example, the antibody or antibody fragment can be directed against or specifically bind to an epitope, an antigenic epitope, or an immunogenic epitope of a C5, C3, C3a, C5a, C5aR, C3aR, C5 convertase, and/or C3 convertase. The term "epitope" as used herein can refer to portions of C5, C3, C3a, C5a, C5aR, C3aR, C5 convertase, and/or C3 convertase having antigenic or immunogenic activity. An "immunogenic epitope" as used herein can include a portion of a C5, C3, C3a, C5a, C5aR, C3aR, C5 convertase, and/or C3 convertase that elicits an immune response in a subject, as determined by any method known in the art. The term "antigenic epitope" as used herein can include a portion of a polypeptide to which an antibody can immunospecifically bind as determined by any method well known in the art.

Examples of antibodies directed against C5, C3, C3a, C5a, C5aR, C3aR, C5 convertase, and/or C3 convertase are known in the art. For example, mouse monoclonal antibodies directed against C3aR can include those available from Santa Cruz Biotechnology, Inc. (Santa Cruz, Calif.). Monoclonal anti-human C5aR antibodies can include those available from Research Diagnostics, Inc. (Flanders, N.J.). Monoclonal anti-human/anti-mouse C3a antibodies can include those available from Fitzgerald Industries International, Inc. (Concord, Me.). Monoclonal anti-human/anti-mouse C5a antibodies can include those available from R&D Systems, Inc. (Minneapolis, Minn.).

In another aspect of the application, the at least one complement antagonist can include purified polypeptide that is a dominant negative or competitive inhibitor of C5, C3, C3a, C5a, C5aR, C3aR, C5 convertase, and/or C3 convertase. As used herein, "dominant negative" or "competitive inhibitor" refers to variant forms of a protein that inhibit the activity of the endogenous, wild type form of the protein (i.e., C5, C3, C3a, C5a, C5aR, C3aR, C5 convertase, and/or C3 convertase). As a result, the dominant negative or competitive inhibitor of a protein promotes the "off" state of protein activity. In the context of the present application, a dominant negative or competitive inhibitor of C5, C3, C3a, C5a, C5aR, C3aR, C5 convertase, and/or C3 convertase is a C5, C3, C3a, C5a, C5aR, C3aR, C5 convertase, and/or C3 convertase polypeptide, which has been modified (e.g., by mutation of one or more amino acid residues, by posttranscriptional modification, by posttranslational modification) such that the C5, C3, C3a, C5a, C5aR, C3aR, C5 convertase, and/or C3 convertase inhibits the activity of the endogenous C5, C3, C3a, C5a, C5aR, C3aR, C5 convertase, and/or C3 convertase.

In some embodiments, the competitive inhibitor of C5, C3, C3a, C5a, C5aR, C3aR, C5 convertase, and/or C3 convertase can be a purified polypeptide that has an amino acid sequence, which is substantially similar (i.e., at least about 75%, about 80%, about 85%, about 90%, about 95% similar) to the wild type C5, C3, C3a, C5a, C5aR, C3aR, C5 convertase, and/or C3 convertase but with a loss of function. The purified polypeptide, which is a competitive inhibitor of C5, C3, C3a, C5a, C5aR, C3aR, C5 convertase, and/or C3 convertase, can be administered to a naive T cell (e.g., $CD45^{hi}CD44^{low}CD4^+$ T cell) expressing C5aR and/or C3aR, to generate a $CD4^+FoxP3^+$ Treg cell.

It will be appreciated that antibodies directed to other complement components used in the formation of C5, C3, C5a, C3a, C5 convertase, and/or C3 convertase can be used in accordance with the method of the present application to reduce and/or inhibit interactions C5a and/or C3a with C5aR and C3aR between dendritic cells and naive $CD4^+$ T cells. The antibodies can include, for example, known Factor B, properdin, and Factor D antibodies that reduce, block, or inhibit the classical and/or alternative pathway of the complement system.

In a further aspect of the present application, the at least one complement antagonist can include RNA interference (RNAi) polynucleotides to induce knockdown of an mRNA encoding a complement component. For example, an RNAi polynucleotide can comprise a siRNA capable of inducing knockdown of an mRNA encoding a C3, C5, C5aR, or C3aR polypeptide in the $CD4^+$ T cells or dendritic cell.

RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation, however the biochemical mechanisms are currently an active area of research. Despite some mystery regarding the mechanism of action, RNAi provides a useful method of inhibiting gene expression in vitro or in vivo.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (I) genetic element(s) having a regulatory role in gene expression, for example, promoters, operators, or enhancers, operatively linked to (2) a "coding"

sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the application has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA Likewise, bases may be modified to block the activity of adenosine deaminase. The RNAi construct may be produced enzymatically or by partial/total organic synthesis, any modified ribonucleotide can be introduced by in vitro enzymatic or organic synthesis.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) Proc Natl Acad Sci USA, 98:9742-9747; Elbashir, et al. (2001) EMBO J, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the Drosophila in vitro system is used. In this embodiment, dsRNA is combined with a soluble extract derived from Drosophila embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

Examples of a siRNA molecule directed to an mRNA encoding a C3a, C5a, C5aR, or C3aR polypeptide are known in the art. For instance, human C3a, C3aR, and C5a siRNA is available from Santa Cruz Biotechnology, Inc. (Santa Cruz, Calif.). Additionally, C5aR siRNA is available from Qiagen, Inc. (Valencia, Calif.). siRNAs directed to other complement components, including C3 and C5, are known in the art.

In other embodiments, the RNAi construct can be in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects, which may be caused by the sequence-independent dsRNA response. In such embodiments, the use of local delivery systems and/or agents, which reduce the effects of interferon or PKR are preferred.

In certain embodiments, the RNAi construct is in the form of a hairpin structure (named as hairpin RNA). The hairpin RNAs can be synthesized exogenously or can be formed by transcribing from RNA polymerase III promoters in vivo.

Examples of making and using such hairpin RNAs for gene silencing in mammalian cells are described in, for example, Paddison et al., Genes Dev, 2002, 16:948-58; McCaffrey et al., Nature, 2002, 418:38-9; McManus et al., RNA, 2002, 8:842-50; Yu et al., Proc Natl Acad Sci USA, 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid can be used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional transcription of a transgene to yield both sense and antisense RNA transcripts of the same transgene in a eukaryotic cell. Accordingly, in certain embodiments, the present application provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of C5, C3, C5aR, and/or C3aR in CD4$^+$ T cells and dendritic cells. Although there have been some safety concerns about the use of lentiviral vectors for gene therapy, self-inactivating lentiviral vectors are considered good candidates for gene therapy as they readily transfect mammalian cells.

It will be appreciated that RNAi constructs directed to other complement components used in the formation of C5, C3, C5a, C3a, C5 convertase, and/or C3 convertase can be used in accordance with the method of the present application to reduce and/or inhibit interactions between C5a and/or C3a with C5aR and C3aR on the FoxP3$^+$ Treg cells. The RNAi constructs can include, for example, known Factor B, properdin, and Factor D siRNA that reduce expression of Factor B, properdin, and Factor D.

Moreover, it will be appreciated that other antibodies, small molecules, and/or peptides that reduce or inhibit the formation of C5, C3, C5a, C3a, C5 convertase, and/or C3 convertase and/or that reduce or inhibit interactions C5a and/or C3a with C5aR and C3aR on naive CD4$^+$ cells can be used as a complement antagonist in accordance with the method of the present application. These other complement antagonists can be administered to the subject and/or naive CD4$^+$ T cells at amount effective to generate CD4$^+$FoxP3$^+$ Treg cells. Example of such other complement antagonists include C5aR antagonists, such as AcPhe[Orn-Pro-D-cyclohexylalanine-Trp-Arg, prednisolone, and infliximab (Woodruff et al., *The Journal of Immunology*, 2003, 171: 5514-5520), hexapeptide MeFKPdChaWr (March et al., *Mol Pharmacol* 65:868-879, 2004), PMX53 and PMX205, and N-R4-dimethylaminophenyl)methyl]-N-(4-isopropylphenyl)-7-methoxy-1,2,3,4-tetrahydronaphthalen-1-carboxamide hydrochloride (W-54011) (Sumichika et al., J. Biol. Chem., Vol. 277, Issue 51, 49403-49407, Dec. 20, 2002), and a C3aR antagonist, such as SB 290157 (Ratajczak et al., Blood, 15 Mar. 2004, Vol. 103, No. 6, pp. 2071-2078).

The at least one complement antagonist can be administered to the naive CD4$^+$ T cells either in vivo or in vitro. In one embodiment, the naive CD4$^+$ T cells can be derived or isolated from a mammalian subject, from a known cell line, or from some other source. One example of a naive CD4$^+$ T cells is a CD45$^{hi}$CD44$^{low}$ CD4$^+$ T cell located in a mammalian subject (e.g., human subject). The CD4$^+$ T cell may be isolated or, alternatively, associated with any number of identical, similar, or different cell types. Where the cell comprises a lymphocyte, for example, the lymphocyte may be associated with a costimulatory cell, such as an APC or DC. By way of example, naive CD4$^+$ T cells (e.g., CD4$^+$ FoxP3$^-$ T cells) for use in the present application can be isolated from a peripheral blood sample taken from a subject.

Once the naive CD4$^+$ T cells are isolated, they can then be cultured in a growth medium with optionally DCs or APCs. "Cultured" and "maintained in culture" are interchangeably used when referring to the in vitro cultivation of cells and include the meaning of expansion or maintenance of a cell population under conditions known to be optimal for cell growth.

A complement antagonist that substantially inhibits C3aR and/or C5aR signaling can be administered to the cultured CD4$^+$ FoxP3$^-$ T cells to induce differentiation of CD4$^+$ FoxP3$^-$ T cells into CD4$^+$ FoxP3$^+$ Treg cells. In one exemplary embodiment, the CD4$^+$FoxP3$^-$ T cells can be cultured for 72 hours in a growth medium comprising a C3a antagonist, a C5a antagonist, C3aR antagonist, and/or C5aR antagonist as well as DCs to generate a population of CD4$^+$ FoxP3$^+$ Treg cells. The cell culture can be maintained under culture conditions including suitable temperature, pH, nutrients, and proper growth factors which favor the in vitro expansion and survival of CD4$^+$FoxP3$^+$ Treg cells. Additional agents that can be added to the cell culture to promote the expansion and survival of CD4$^+$FoxP3$^+$ Treg cells include, but are not limited to, anti-CD3/28 stimulating agents (e.g., anti-CD3/CD28 Dynabead activation beads) TGF-β, and IL-2.

The CD4$^+$FoxP3$^+$ Treg cells produced by methods of the present application have the immunoregulatory characteristics of wild type Treg cells. Accordingly, it is further contemplated that the CD4$^+$FoxP3$^+$ Treg cells generated by the methods of the application can be used to prevent local and systemic organ and tissue destruction in cell therapies aimed at alleviating T cell mediated disorders or diseases.

The term "T cell mediated disease" or "T cell mediated disorder" refers to diseases and disorders in which an aberrant immune reaction involves T cell-mediated immune mechanisms, as opposed to humoral immune mechanisms. T cell mediated diseases contemplated by the present application also include T cell mediated autoimmune diseases or disorders. The language "autoimmune disorder" is intended to include disorders in which the immune system of a subject reacts to autoantigens, such that significant tissue or cell destruction occurs in the subject. The term "autoantigen" is intended to include any antigen of a subject that is recognized by the immune system of the subject. The terms "autoantigen" and "self-antigen" are used interchangeably herein. The term "self" as used herein is intended to mean any component of a subject and includes molecules, cells, and organs. Autoantigens may be peptides, nucleic acids, or other biological substances.

Thus, the methods of the application pertain to treatments of immune disorders in which tissue destruction is primarily mediated through activated T cells and immune cells. For example, the methods of the present application can be used in the treatment of autoimmune conditions or diseases, such as inflammatory diseases, including but not limited to achlorhydra autoimmune active chronic hepatitis, acute disseminated encephalomyelitis, acute hemorrhagic leukoencephalitis, Addison's disease, agammaglobulinemia, alopecia areata, Alzheimer's disease, amyotrophic lateral sclerosis, ankylosing spondylitis, anti-gbm/tbm nephritis, antiphospholipid syndrome, antisynthetase syndrome, aplastic anemia, arthritis, atopic allergy, atopic dermatitis, autoimmune cardiomyopathy, autoimmune hemolytic anemia, autoimmune hepatitis, autoimmune inner ear disease, autoimmune lymphoproliferative syndrome, autoimmune peripheral neuropathy, autoimmune polyendocrine syndrome, autoimmune progesterone dermatitis, autoimmune thrombocytopenia purpura, autoimmune uveitis, balo disease/balo concentric sclerosis, Bechets syndrome, Berger's disease, Bickerstaff's encephalitis, blau syndrome, bullous pemphigoid, Castleman's disease, Chagas disease, chronic fatigue immune dysfunction syndrome, chronic inflammatory demyelinating polyneuropathy, chronic lyme disease, chronic obstructive pulmonary disease, Churg-Strauss syndrome, cicatricial pemphigoid, coeliac disease, Cogan syndrome, cold agglutinin disease, cranial arteritis, crest syndrome, Crohns disease, Cushing's syndrome, Dego's disease, Dercum's disease, dermatitis herpetiformis, dermatomyositis, diabetes mellitus type 1, Dressler's syndrome, discoid lupus erythematosus, eczema, endometriosis, enthesitis-related arthritis, eosinophilic fasciitis, epidermolysis bullosa acquisita, essential mixed cryoglobulinemia, Evan's syndrome, fibrodysplasia ossificans progressive, fibromyalgia, fibromyositis, fibrosing aveolitis, gastritis, gastrointestinal pemphigoid, giant cell arteritis, glomerulonephritis, Goodpasture's syndrome, Graves' disease, Guillain-barrésyndrome (gbs), Hashimoto's encephalitis, Hashimoto's thyroiditis, henoch-schonlein purpura, hidradenitis suppurativa, Hughes syndrome, inflammatory bowel disease (IBD), idiopathic inflammatory demyelinating diseases, idiopathic pulmonary fibrosis, idiopathic thrombocytopenic purpura, iga nephropathy, inflammatory demyelinating polyneuopathy, interstitial cystitis, irritable bowel syndrome (ibs), Kawasaki's disease, lichen planus, Lou Gehrig's disease, lupoid hepatitis, lupus erythematosus, ménière's disease, microscopic polyangiitis, mixed connective tissue disease, morphea, multiple myeloma, multiple sclerosis, myasthenia gravis, myositis, narcolepsy, neuromyelitis optica, neuromyotonia, occular cicatricial pemphigoid, opsoclonus myoclonus syndrome, ord thyroiditis, Parkinson's disease, pars planitis, pemphigus, pemphigus vulgaris, pernicious anaemia, polymyalgia rheumatic, polymyositis, primary biliary cirrhosis, primary sclerosing cholangitis, progressive inflammatory neuropathy, psoriasis, psoriatic arthritis, raynaud phenomenon, relapsing polychondritis, Reiter's syndrome, rheumatoid arthritis, rheumatoid fever, sarcoidosis, schizophrenia, Schmidt syndrome, Schnitzler syndrome, scleritis, scleroderma, Sjögren's syndrome, spondyloarthropathy, sticky blood syndrome, still's disease, stiff person syndrome, sydenham chorea, sweet syndrome, takayasu's arteritis, temporal arteritis, transverse myelitis, ulcerative colitis, undifferentiated connective tissue disease, undifferentiated spondyloarthropathy, vasculitis, vitiligo, Wegener's granulomatosis, Wilson's syndrome, Wiskott-Aldrich syndrome as well as hypersensitivity reactions of the skin, atherosclerosis, ischemia-reperfusion injury, myocardial infarction, and restenosis. The methods of the present application can also be used for the prevention or treatment of the acute rejection of transplanted organs where administration of a therapeutic described herein, may occur during the acute period following transplantation or as long-term post transplantation therapy.

In a method of treating a T cell mediated disease or disorder in a subject, a therapeutically effective amount of the inventive $CD4^+$ $FoxP3^+$ Treg cells to the subject. The therapeutically effective amount of $CD4^+$ $FoxP3^+$ Treg cells to be administered to a subject can be determined by a practitioner based upon such factors as the levels of $CD4^+$ $FoxP3^+$ Treg cells induction achieved in vitro, the mode of administration, and/or the particular T cell mediated disease to be treated.

The $CD4^+FoxP3^+$ Treg cells may originate from a subject into which they are implanted (reimplantation) or from elsewhere (transplantation). In some aspects, a subject is administered $CD4^+$ $FoxP3^+$ Treg cells derived from the subject's own body because the risk of transmission of an infection such as HIV is eliminated and the risk of triggering an immune system-mediated rejection reaction is reduced.

In general, the $CD4^+FoxP3^+$ Treg cells are administered (e.g., implanted) into the mammalian subject by methods well known in the art. The $CD4^+FoxP3^+$ Treg cells of the present application may be introduced into the subject by any suitable route whether that route is enteral or parenteral, for example, intravenous or intramuscular. In one exemplary embodiment, $CD4^+FoxP3^+$ Tregs cells are administered directly to an area of a T cell mediated disease.

In another embodiment of the application, the naive $CD4^+$ T cell can comprise a naive $CD4^+$ T cell in the subject and the complement antagonist can be used to treat a T cell mediated disease in the subject. The at least one complement antagonist can be administered to the subject to treat the T cell mediated disease in the subject using any one or combination of known techniques.

In one aspect of the application, the complement antagonist can be administered directly or locally to a site of T cell mediated disease in the subject. Local or direct administration of the complement antagonist into and/or about the periphery of the disease site is advantageous because the complement antagonist localizes at the disease site being treated and does not substantially affect the subject's innate complement system.

In another aspect of the application, the complement antagonist can be administered to the subject systemically by, for example, intravenous, intraarterial, intraperitoneal, intramuscular, subcutaneous, intrapleural, intrathecal, oral or nasal route, to treat the T cell mediated disease or related disorder in the subject. When administered systemically, the complement antagonist can be targeted to a disease site to ensure that the complement antagonist does not adversely affect other normal cells expressing C5aR and/or C3aR, and to potentially mitigate adverse systemic effects on the subject's complement system. Several systems have been developed in order to restrict the delivery of the complement antagonist to the disease site. With the identification of cells specific receptors and antigens on mammalian cells, it is possible to actively target the complement antagonist using ligand or antibody bearing delivery systems. Alternatively, the complement antagonist can be loaded on a high capacity drug carriers, such as liposomes or conjugated to polymer carriers that are either directly conjugated to targeting proteins/peptides or derivatised with adapters conjugated to a targeting moiety.

Examples of antibodies which can be potentially conjugated to the complement antagonist to target the complement antagonist to the T cell mediated disease site include, but are not limited to, anti-CD20 antibodies (e.g., Rituxan, Bexxar, Zevalin), anti-Her2/neu antibodies (e.g., Herceptin), anti-CD33 antibodies (e.g., Mylotarg), anti-CD52 antibodies (e.g., Campath), anti-CD22 antibodies, anti-CD25 antibodies, anti-CTLA-4 antibodies, anti-EGF-R antibodies (e.g. Erbitux), anti-VEGF antibodies (e.g. Avastin, VEGF Trap) anti-HLA-DR10β antibodies, anti-MUC1 antibodies, anti-CD40 antibodies (e.g. CP-870,893), anti-Treg cell antibodies (e.g., MDX-010, CP-675,206), anti-GITR antibodies, anti-CCL22 antibodies, and the like.

The complement antagonist, whether administered locally and/or systemically, can also be provided in a pharmaceutically acceptable composition. The phrase "pharmaceutically acceptable" should be understood to mean a material which is not biologically or otherwise undesirable, i.e., the material may be incorporated into an antiviral composition and administered to a subject without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. Sterile phosphate-buffered saline is one example of a pharmaceutically acceptable carrier. Other suitable carriers are well-known to those in the art. See, for example, REMINGTON'S PHARMACEUTICAL SCIENCES, 19th Ed. (1995), and later editions.

In general, the dosage of the at least one complement antagonist will vary depending upon such factors as the subject's age, weight, height, sex, general medical condition and previous medical history. Typically, it is desirable to provide the subject with a dosage of the at least one complement antagonist which is in the range of from about 1 pg/kg to 10 mg/kg (amount of agent/body weight of patient), although a lower or higher dosage also may be administered as circumstances dictate. The specific dosage or amount of complement antagonist administered to a naive CD4+ T cell (e.g., a human CD45$^{hi}$CD4$^{low}$ CD4+ T cell) will be that amount effective to reduce or inhibit C5a/C3a-C5aR/C3aR interactions.

In an example of the method, a therapeutically effective amount of a pharmaceutical composition comprising a first antibody directed against C3aR and a second antibody directed against C5aR can be administered to a naive CD4+ T cell or a subject having a T cell mediated disease. The pharmaceutical composition can be administered to the subject intravenously using, for example, a hypodermic needle and syringe. Upon administration of the pharmaceutical composition to the subject, the first and second antibodies can respectively bind to C3aR and C5aR on at least one T lymphocyte. Binding of the first and second antibodies can effectively inhibit or reduce the ability of C3a and C5a to respectively bind C3aR and C5aR. Consequently, C5a/C3a-05aR/C3aR signaling can be reduced or eliminated such that the at least one naive CD4+ T cell undergoes differentiation into a CD+FoxP3+ Treg cell.

The following examples are for the purpose of illustration only and are not intended to limit the scope of the claims, which are appended hereto.

Example 1

This Example shows that quiescence of C3aR/C5aR signaling between DC-CD4+ cells causes suppression of T cell activation by simultaneously inducing potent FoxP3+ iTregs. As a first test of how DC-CD4+ cell C3aR/C5aR signal transduction impacts iTreg induction, we stimulated naive CD4+ cells from mice in which the FoxP3 gene promoter is linked to GFP (FoxP3-GFP mice) with anti-CD3, IL-2 and WT DCs without TGF-β1 in the presence of C3aR/C5aR pharmaceutical antagonists (C3aR-A/C5aR-A), anti-C3a/C5a mAbs, or controls. Both treatments induced FoxP3+ cells (FIG. 2A). The sorted GFP cells failed to produce IL-2 following PMA and ionomycin treatment and were anergic to anti-CD3/28 stimulation consistent the properties of iTregs. They conferred ~4-fold> suppression in mixtures of ova-primed DCs and CellTracker Red-labeled OT-II cells than sorted GFP cells conventionally induced with exogenous TGF-β1 (FIG. 2B). Stimulation of naive C3aR$^{-/-}$C5aR$^{-/-}$ or C3$^{-/-}$C5$^{-/-}$ CD4+ cells with anti-CD3, DCs and IL-2 similarly resulted in the induction of FoxP3+ cells with potent suppressor function (FIG. 2B). Addition of C5a blocked iTreg induction and suppressor function when naive C3$^{-/-}$C5$^{-/-}$ CD4+ cells were stimulated (FIG. 2B).

Analyses of day 3 supernatants of mixtures that contained C3aR/C5aR antagonized FoxP3-GFP CD4+ cells or C3aR$^{-/-}$C5aR$^{-/-}$ CD4+ cells showed abundant TGF-β1 as well as IL-10, in contrast to little of either cytokine but IL-6 in WT CD4+ cell containing mixtures (FIG. 2C). Culturing of flow sorted DCs and CD4+ cells showed that both cytokines were being produced by both partners, more IL-10 by the CD4+ cells and more TGF-β1 by the DCs. In contrast to stimulating naive WT cells with anti-CD3/28 plus IL-2 without DCs which generated IL-6, identical stimulation of naive C3aR$^{-/-}$C5aR$^{-/-}$ cells generated TGF-β1/IL-10, albeit 12-/20-fold less than when WT DCs were present. Inclusion of C3aR$^{-/-}$C5aR$^{-/-}$ DCs [which do not produce C3a/C5a] increased TGF-β1/IL-10 production and iTreg numbers about 2-fold more than inclusion of WT DCs (FIG. 2D), indicating that while absent C3aR/C5aR transduction in stimulated naive CD4+ cells is sufficient to induce TGF-β1/IL-10, absent C3aR/C5aR transduction in interacting DCs markedly augments TGF-β1/IL-10 production by both partners.

To establish whether the endogenous TGF-β1 that is produced in the absence of C3aR/C5aR signaling promotes iTreg induction, we incubated naive C3aR$^{-/-}$C5aR$^{-/-}$ CD4+ cells with anti-CD3, IL-2, and DCs in the presence and absence of an anti-TGF-β1 blocking mAb. The presence of the mAb abrogated FoxP3+ cell induction (FIG. 2E). To establish whether the endogenous TGF-β1 enters into an autocrine signaling loop that amplifies endogenous TGF-β1 production, we added specific antagonists of TGF-βR1, or Smad3, a requisite partner of Smad4 and transcription factor (TF) essential for TGF-β1 gene transcription. Both agents markedly reduced TGF-β1 (FIG. 2F) and IL-10 production in both the CD4+ cells and DCs (FIG. 2G) and essentially abrogated FoxP3+ cell induction (FIG. 2E), indicating that IL-10 production and FoxP3+ cell induction are dependent on auto-inductive TGF-β1 signaling.

Comparison of the phenotypes of WT DCs that derived from the co cultures with C3aR$^{-/-}$ C5aR$^{-/-}$ or WT CD4+ cells (without added TGF-β1) showed that DCs incubated with stimulated C3aR$^{-/-}$C5aR$^{-/-}$ CD4+ cells (FIG. 3A) expressed 11-fold lower levels of costimulatory B7-1, 10-fold lower costimulatory B7-2, and 2.5-fold lower levels of CD40, while only small changes (increases) in coinhibitory PD-L1 (P=0.07) and ICOS-L (P=0.013) were apparent. Similarly FoxP3+ cells deriving from the C3aR$^{-/-}$C5aR$^{-/-}$ CD4+ cells expressed markedly decreased levels of costimulatory CD28 and CD40 ligand (CD40L), similar levels of coinhibitory PD-1 and ICOS, and increased levels of stably surface expressed CTLA-4 (FIG. 3A). Thus, there is a direct correlation between the absence of C3aR/C5aR signal transduction and the downregulation of co-stimulatory molecule expression on DCs and CD4$^+$ cells [consistent with our earlier results] and the upregulation of immunosuppressive CTLA-4 on CD4$^+$ cells. Comparison of iTregs conventionally generated with exogenous TGF-β1 to those generated by C3aR/C3aR antagonism showed 3-6-fold higher costimulatory molecule expression (FIG. 3B) more closely resembling the phenotype of Th17 effector cells.

To determine the significance of the changes in surface phenotypes of DCs and CD4$^+$ cells in the absence of C3aR/C5aR signals on the induction of FoxP3$^+$ T cells derived from the naive C3aR$^{-/-}$C5aR$^{-/-}$ responder CD4$^+$ cells, we added anti-PD-L1 or anti-ICOS-L mAb to the co-cultures. The immunological blockade in both cases caused marked inhibition of both TGF-β/IL-10 production and FoxP3$^+$ cell induction (FIG. 3C). Comparable results were obtained when we substituted PD-L1$^{-/-}$ DCs for WT DCs or naive PD-1$^{-/-}$ or ICOS$^{-/-}$ CD4$^+$ cells for naive WT CD4$^+$ cells (FIG. 3D). Interfering with CTLA-4/CD80-CD86 interactions also inhibited iTreg induction (FIG. 3C). Collectively, these findings that pertain in the absence of C3aR/C5aR signaling are consistent with reports that the interactions of PD-1/PD-L1, ICOS/ICOS-L as well as CTLA-4/CD80-CD86 all play roles in amplifying TGF-β1/IL-10 production and inducing iTregs For C3aR/C5aR signaling to be absent, local complement production by interacting DCs and CD4$^+$ cells must not occur or be suppressed. The above findings connecting absent C3aR/C5aR signaling with iTreg commitment, together our previous findings connecting potentiated C3aR/C5aR signaling with Th1 and Th17 commitment suggested that the divergent effects of TGF-β1 vs IL-6 on naive CD4$^+$ cell differentiation might be mechanistically linked to opposing effects on local complement production by CD4$^+$ cells. As a first test of this, we incubated anti-CD3/CD28 stimulated CD4$^+$ cells in the presence and absence of TGF-β1. The added TGF-β1 abolished transcription of all the complement genes connected with C3aR/C5aR signaling (FIG. 3E) and induced FoxP3$^+$ cells (FIGS. 2A, D, E). To test how IL-6 affects CD4$^+$ cell complement production, we added IL-6 to naive CD4$^+$ cells. In contrast to TGF-β1, IL-6 (or IL-6 in combination with TGF-β1) upregulated complement mRNA transcription (FIG. 3F). Consistent with the IL-6 induction of naive CD4$^+$ cell complement gene transcription, IL-6 (as well as IL-6 plus TGF-⊕1) evoked DC-CD4$^+$ cell C3a/C5a production (FIG. 3G) and upregulated C3aR/C5aR expression (FIG. 3H), whereas TGF-β1 alone did neither. In accordance with the absence of C3a/C5a production and consequent C3aR/C5aR signaling being required for iTreg induction, adding IL-6 or C5a to anti-CD3/28 stimulated naive CD4$^+$ cells (FIG. 3I) inhibited FoxP3 mRNA transcription. These data thus argue that DC control of naive CD4$^+$ cell C3aR/C5aR signaling is one switch through which TGF-β1 alone vs IL-6 (or IL-6 plus TGF-β1 in combination) bias between iTreg vs Th1/Th17 effector cell commitment.

To establish whether the above findings apply in vivo, we used four systems: 1) In the first, we tested whether C3aR/C5aR antagonism in CD4$^+$ cells, in recipients, or both is(are) involved in iTreg induction. We adoptively transferred (unfractionated) OT-II cells or C3aR$^{-/-}$C5aR$^{-/-}$ OT-II cells iv into WT or C3aR$^{-/-}$C5aR$^{-/-}$ recipients, two days after which we immunized recipient mice with ovalbumin (ova) in CFA. Five days thereafter, more ova specific FoxP3$^+$ OT-II cells (identified by anti-OT-II TCR mAbs) were present in the spleen when either the recipient or OT-II cells were C3aR/C5aR deficient and most (2.5-fold more) when both were C3aR/C5aR deficient. The production of TGF-β1 and IL-10 by cultured spleen cells of the C3aR$^{-/-}$C5aR$^{-/-}$ to C3aR$^{-/-}$C5aR$^{-/-}$ and WT to WT donor-recipient combinations showed the same pattern. To document that absent C3aR/C5aR signaling in naive CD4$^+$ cells is essential, we adoptively transferred CFSE-labeled naive (CD25$^-$) OT-II cells as a source of effectors into WT recipients. Two days later, at the time of ova immunization, we co-administered Cell-Tracker Red naive (CD25$^-$) Daf1$^{-/-}$ OT-II cells (in which DC C3aR/C5aR signaling is potentiated) or CellTracker Red naive (CD25$^-$) C3aR$^{-/-}$C5aR$^{-/-}$ OT-II cells (in which C3aR/C5aR signaling is precluded) as a source of iTregs. Five days later CellTracker Red labeled C3aR$^{-/-}$C5aR$^{-/-}$ OT-II cells but not CellTracker Red labeled Daf1$^{-/-}$ OT-II cells were CD25$^+$ (FIG. 4A). The CellTracker Red labeled C3aR$^{-/-}$C5aR$^{-/-}$ OT-II cells suppressed proliferation of the CFSE labeled responder OT-II cells 9-fold more efficiently than the CellTracker Red labeled Daf1$^{-/-}$ OT-II cells (FIG. 4B). A repeat experiment utilizing WT mice in place of Daf1$^{-/-}$ yielded the same results. To document that absent C3aR/C5aR signaling in recipients is essential, we adoptively transferred CellTracker Violet labeled CD25$^-$ OT-II cells as a source of T effectors to WT or C3aR$^{-/-}$C5aR$^{-/-}$ recipients. Two days later, at the time of immunization, we adoptively transferred CD25$^-$ OT-II FoxP3-GFP cells. Five days later, 18% of splenic CD4$^+$ cells were FoxP3$^+$ cells in C3aR$^{-/-}$C5aR$^{-/-}$ recipients as compared to 10% in WTs (FIG. 4C). Additionally, 10-fold greater suppression of CellTracker Violet dilution occurred in the C3aR$^{-/-}$C5aR$^{-/-}$ recipient than in the WT recipient (FIG. 4D).

In the second system, we compared the in vivo suppressive activity of iTregs generated by C3aR/C5aR antagonism (no added TGF-β1) to that of iTregs conventionally generated (with added TGF-β1). We adoptively transferred 10$^6$ CellTracker Red-labeled naive (CD25$^-$) OT-II cells to WT mice. Two days later, we immunized the mice with ova in CFA and at the same time transferred equal numbers of sorted green (FoxP3$^+$) cells derived from stimulated naive CD25$^-$FoxP3-GFP CD4$^+$ cells alternatively treated with C3aR-A/C5aR-A or with TGF-β1. Cell-Tracker Red dilution of the responder OT-II cells in lymph nodes 5 days later showed that sorted (green) FoxP3$^+$ cells generated with C3aR-A/C5aR-A exerted >2 fold more suppression than those generated with exogenous TGF-β1 (FIG. 4E).

We designed a third model to compare the suppressive function of antigen specific vs antigen non-specific iTregs generated by C3aR/C5aR antagonism. We transferred 1×10$^6$ CD25$^-$ OT-II cells to WT recipients as a source of responders. At the same time, we co transferred increasing numbers of iTregs generated by C3aR-A/C5aR-A treatment of either 1) CellTracker Violet labeled naive CD25$^-$ OT-II (specific for ova) CD4$^+$ cells, or 2) nonrelated CFSE labeled naive CD25$^-$2D2 (specific for MOG$_{35-55}$) CD4$^+$ cells. One day thereafter, we immunized both recipients with ova in CFA. Flow cytometry of spleen cells five days later gating on CFSE and CellTracker Violet (FIG. 4F) showed that ova specific CD25$^+$ OT-II cells (generated by anti-CD3, IL-2 and C3aR/C5aR antagonism) exerted robust suppression (reduced dividers to 11% at an injection ratio of 4:1) whereas the TCR nonspecific CD25$^+$ (FoxP3$^+$) 2D2 iTregs generated the same way exerted less suppression (reduced dividers to 65%). While 2D2 cells express a clonal TCR for MOG$_{35-55}$, they were activated ex vivo with anti-CD3. Consequently, while they exerted less suppressive activity than OT-II cells which express a clonal TCR for ova$_{323-339}$, their suppressive activity was similar to FoxP3$^+$ Tregs induced from polyclonal naive (CD25$^-$)CD4$^+$ cells (see FIG. 4A). To study whether iTregs generated by C3aR/C5aR antagonism maintained their phenotype and suppressive capacity, iTregs were induced for 3 days with C3aR-A/C5aR-A as before and cells were sorted for FoxP3$^+$ expression. Following an additional 10 days of incubation with anti-CD3/28 plus IL-2, >95% remained FoxP3$^+$ and resorted cells retained their full suppressive activity.

In the fourth system, we evaluated how efficacy of iTreg induction by C3aR/C5aR antagonism for ameliorating autoimmunity using the EAE model of multiple sclerosis. We first performed studies with Rag-2$^{-/-}$ recipients devoid of nTregs and T effector cells to obviate any influence of 1) endogenous nTregs and/or iTregs and 2) any possibility that FoxP3$^+$ cells themselves are not being measured. To prepare donor T effector and iTregs, we immunized FoxP3-GFP mice with MOG$_{35-55}$ in CFA. After establishment of disease (clinical score>2), we isolated CD4$^+$ cells from lymph nodes and the spleen and removed green cells (endogenous nTregs and iTregs) by flow sorting. We then isolated CD25$^-$ cells from the nongreen cell population. We treated half of these cells with C3aR-A/C5aR-A to produce green iTregs. In one set of Rag-2$^{-/-}$ recipients (5 mice), we administered 1×10$^6$ cells from the other half of the nongreen cells (containing T effector cells) by themselves. In a second set of the Rag-2$^{-/-}$ recipients (5 mice), we administered an identical aliquot (1×10$^6$) of the same effector cell population together with 1×10$^6$ of the rested C3aR-A/C5aR-A induced green iTregs. Monitoring the animals thereafter showed that while the Rag-2$^{-/-}$ recipients that received untreated nongreen CD4$^+$ cells containing T effectors by themselves showed progressive weakness and weight loss, the Rag-2$^{-/-}$ mice that additionally received C3aR-A/C5aR-A induced green iTregs showed markedly less disease which gradually declined and their weights recovered (FIG. 5AB). At day 7 (FIG. 5C) post adoptive transfer, green cells were detectable in lymph nodes and spinal cords of these mice but not in those that received the untreated nongreen population by itself. Identical results were obtained in a repeat experiment in which we pre-immunized the Rag-2$^{-/-}$ recipient mice with MOG$_{35-55}$ in CFA.

Armed with the above control data, we next examined how DC-CD4$^+$ cell C3aR/C5aR signaling is interconnected with iTregs and EAE disease severity in immune sufficient mice. We induced EAE in WT and in C3aR$^{-/-}$C5aR$^{-/-}$ mice. Ten days later, less IFN-γ and more TGF-β1/IL-10 and more FoxP3$^+$ cells (FIG. 5D) were present in lymph nodes of C3aR$^{-/-}$C5aR$^{-/-}$ mice than in WTs. Splenic CD4$^+$ cells from C3aR$^{-/-}$ C5aR$^{-/-}$ mice (isolated by CD4$^+$ negative selection followed by sorting on CD4$^+$ CD25$^+$ cells) contained 2-fold more FoxP3$^+$ cells and conferred 5-fold > suppression than those from WTs (FIG. 5E). In a second experiment, we established EAE in FoxP3-GFP mice and treated sick mice (scores >2) with adoptively transferred FoxP3$^+$ (green) cells generated ex vivo by incubating naive (CD25$^-$) CD4$^+$ cells from FoxP3-GFP mice with C3aR-A/C5aR-A. Following adoptive transfer of 1×10$^6$ green FoxP3$^+$ cells, clinical scores decreased (FIG. 5F) and weights increased. At days 7 and 14 post adoptive transfer, green cells were detectable in lymph nodes and spinal cords.

To test whether C3aR/C5aR antagonism is more effective than exogenous TGF-β1 in preparing human iTregs, we incubated human CD45RA$^+$CD25$^-$CD4$^+$ cells with anti-CD3, IL-2 and C3aR-A/C5aR-A for 3 days and quantified FoxP3$^+$ cells. After verifying that CD25$^{hi}$ cells were >95% FoxP3$^+$ using multiple anti-FoxP3 Abs and that PMA plus ionomycin treatment of the sorted CD25$^+$ cells produced no IL-2 and that the sorted cells were anergic compared to identically treated naive CD4$^+$ cells, we added an equal number of sorted CD25$^+$ cells (that stained FoxP3$^+$ in a parallel aliquot) prepared this way or prepared with exogenous TGF-β1 to mixtures of DCs, anti-CD3, and CFSE-labeled CD25$^-$CD4$^+$ cells from the same individual. The CD25$^+$ (FoxP3$^+$) cells prepared by C3aR/C5aR antagonism exerted robust suppression (FIG. 5G) whereas those prepared with TGF-β1 had little effect. As found with mouse cells (FIG. 3B), phenotyping of the iTregs prepared with TGF-β1 showed costimulatory molecules, while those prepared by C3aR/C5aR antagonism did not.

The above data provide several new insights concerning how T cell responses are controlled: 1) They demonstrate that absent C3aR/C5aR signal transduction in naive CD4$^+$ cells during their interaction with DC partners that do not produce C3a/C5a leads to the induction of iTregs. Taken together our findings show that DC control of this GPCR signaling in naive CD4$^+$ cells serves as one switch which regulates whether tolerogenic or effector T cell responses are mounted in response to peptide bearing DCs. 2) They provide a molecular mechanism for the findings that TGF-β1 biases toward iTreg lineage commitment, whereas IL-6 or IL-6 plus TGF-β1 bias toward Th1 and Th17 lineage commitment. 3) They explain the source of TGF-β1 that evokes iTreg induction and that of IL-10 which is involved in Treg immunosuppressive function. 4) They demonstrate that while iTregs that arise in the absence of C3aR/C5aR signaling do not express costimulatory molecules, iTregs induced by exogenously added TGF-β1 do, and potentially explain one mechanism of their more robust suppressive function and greater stability. 5) They provide more information on the functional effects of coupling of B7 family co-inhibitory molecules to their CD4$^+$ cell counter-receptors. 6) They open a previously unrecognized avenue by which iTregs can be induced ex vivo as well as in vivo.

Materials and Methods

Reagents and Antibodies

Murine C5a was from Cell Sciences, Inc (Canton, Me.). Mouse C3a and C5a mAbs were from R&D Systems (Minneapolis, Minn.). Mouse IL-2, IL-10, IFN-γ, human IL-2, IL-10, IFN-γ and human TGF-β1 were from Prospec Bio (Rehovot, Isreal). Antibodies against mouse B7-1, B7-2, C5aR, PD-1, ICOSL, ICOS, PD-L1, and CTLA-4 were from BD Biosciences (San Diego, Calif.). Anti-CD40L mAb was from BioExpress (West Lebanon, N.H.). Anti-C3aR was purchased from Santa Cruz Biotech (Santa Cruz, Calif.). Mouse and Human anti-FoxP3 mAbs and Treg staining kits were purchased from eBiosciences (San Diego, Calif.). CFSE, CellTracker Red, and CellTracker Violet were purchased from Invitrogen (San Diego, Calif.) and used per the manufacturer's instructions.

Animals

C57BL/6, OT-II (specific for OVA$_{323-339}$ plus I-A$^b$), Rag2$^{-/-}$, C3$^{-/-}$, and C5 deficient mice were from Jackson labs (Bar Harbor, Me.). C3$^{-/-}$ mice and C3aR$^{-/-}$ and C5aR$^{-/-}$ l were gifts of Dr. Michael Carroll and Dr. Craig Gerard (Harvard Medical School and Childrens Hospital, Boston, Mass.). C5$^{-/-}$C3$^{-/-}$ mice were generated by crossing C5 deficient B10.2 mice with C57BL/6 congenic C3$^{-/-}$ mice. C5$^{+/+}$C3$^{+/+}$ littermates used as controls displayed comparable results to the studies with C57BL/6 mice as controls. All studies were approved by the Case Western Reserve University Institutional Animal Care and Use Center (IACUC).

RNA Purification, cDNA Synthesis, and qPCR

Cells were purified for 5 min at 20° C. using Trizol (Invitrogen, Carlsbad, Calif.) according to the manufacturer. When C3aR and C5aR mRNAs were analyzed, preparations were treated with DNase I (standard protocol) to remove genomic DNA. cDNAs were synthesized by incubating 20 µl of mRNAs in Sprint PowerScript Single Shots (Clontech, Mountain View, Calif.). Ten µl of diluted cDNA were mixed with 2 µl of primer and 10 µl SYBR green master mix (Applied Biosystems, Foster City, Calif.) and assayed in triplicate on an ABI prism 7000 cycler. In all assays fold increases are relative to each basal level and standardized to Actin.

Murine DCs and T Cell Isolations

CD4$^+$ T cells were isolated from spleens and lymph nodes using the CD4$^+$ negative selection cocktail from Miltenyi (Bergisch Gladbach, Germany) per the manufacturer's instructions. CD11c$^+$ cells were isolated from spleens using the positive selection cocktail from Miltenyi per the manufacturer's instructions. Both were purified using the Automacs Pro.

Immunizations and Flow Cytometry

Mice were immunized s.c. with OVA$_{323-339}$ or MOG$_{35-55}$ peptide as described. All antibodies unless otherwise noted were purchased from BD Biosciences (San Diego, Calif.), stained cells analyzed on a Becton-Dickinson LSR I or II.

Anti-CD3 and Anti-CD28 Stimulations

Cells were stimulated three different ways: 1) 1 µg/ml anti-CD3 and/or anti-CD28 (BD Biosciences, San Diego, Calif.) in complete RPMI 1640+10% FBS; 2) 1 µg/ml anti-CD3 and CD11c$^+$ DCs in complete RPMI 1640; or 3) with 1:1 ratio of CD3/CD28 coated Dynabeads (Invitrogen) per the manufacturer's instructions.

FoxP3$^+$ Staining Assays

For both Human and Murine Treg staining assays, the relevant FoxP3$^+$ T regulatory staining kits (236A/E7 for Human and FJK-16s for mouse) were purchased from eBiosciences and used per the manufacturer's instructions.

Murine Treg Suppression Assays

CFSE-labeled CD4$^+$CD25$^-$ T cells ($1\times10^6$) sorted by FACS were stimulated with $1\times10^5$ autologous CD11c$^+$ DCs and 1 µg/mL anti-CD3 mAb (BD Biosciences) alone or with various numbers of suppressor cells. The cells were cultured for 3 days in 96-well flat-bottom plates and CFSE dilution was analyzed by FACS.

ELISAs

For C5a, C3a, IL-2, IL-10, and IL-6, capture and biotinylated detection Ab pairs were purchased from BD Biosciences. For TGF-β1, the human Ab pair (cross reacts with mouse) was purchased from eBiosciences. 96-well Costar 3590 plates (Corning, N.Y.) were coated with 100 µl of 2 µg/ml capture Ab (either C5a, C3a, IL-2, IL-10, IL-6 or TGF-β1) overnight at 4° C. Following washing, 100 µl of culture supernatants (acid activated in the case of TGF-β1) were added to the plates and again were incubated overnight at 4° C. Well were washed, then 100 of 2 µg/ml biotinylated detection Ab were added and plates were incubated at RT for 4 hr. The plates were then washed and streptavidin-conjugated HRP was added to each well for 30 min. Wells were then washed 7 times and 60 µl of TMB substrate (Pierce, Rockford, Ill.) was added to the plates. Reactions were terminated using 1N $H_2SO_4$ and plates were read using a SpectraMax M2 fluorimeter.

Induction and Evaluation of EAE

Animals were injected sc with 100 µg of MOG$_{33-35}$ in CFA containing 400 µg of *Mycobacterium tuberculosis* H37RA (Difco, Detroit, Mich.). Upon immunization and two days later, 200 ng of pertussis toxin (List Biological Labs Inc., Campbell, Calif.) was injected ip. Mice were weighed and scored for neurological deficits daily: 0=no disease; 1=decreased tail tone or slightly clumsy gait; 2=tail atony; 3=limb weakness; 4=limb paralysis; 5=moribund state.

Adoptive Transfer of T Cells 10 days after priming 8-12 wk old female mice with MOG$_{35-55}$ in CFA containing H37RA, $4\times10^6$ washed CD4$^+$ CD25$^-$ cells were administered iv via tail vein into WT or Rag2$^{-/-}$ recipients. Clinical scores and weights were monitored as above.

Human Treg Isolation

The acquisition of blood products was approved according to the policies of the University Hospitals Cleveland Case Medical Center in accordance with the Declaration of Helsinki. Peripheral blood mononuclear cells (PBMCs) were obtained from 5 to 10 mL blood from healthy donors. Written informed consent was obtained from all donors in accordance with the Declaration of Helsinki. PBMCs were prepared over Histopaq gradient centrifugation (Sigma Aldrich, St Louis, Mo.) and CD4 as well as blood DCs were purified as follows. For FACS, CD4$^+$ cells were enriched over the AutoMACS Pro Separator by positive selection with human CD4 microbeads (Miltenyi Biotec, Auburn, Calif.) and DCs were isolated by positive selection using the Blood Dendritic Cell Isolation Kit II (Miltenyi Biotec, Auburn, Calif.). The cells were labeled with CD4 FITC, CD25 PE, CD45RA PE-Cy5.5 (all Invitrogen, Carlsbad, Calif.) and CD127 Alexa Fluor 647 (BD Biosciences, San Jose, Calif.). The FACSAria flow cytometer was used to sort Tregs by gating on the top 2% CD25$^{hi}$ and non-Tregs by gating on CD4$^+$CD25$^-$ CD127$^+$CD45RA$^+$ cells.

Human Treg Assays

CFSE-labeled CD4$^+$CD25$^-$ T cells ($1\times10^6$) sorted by FACS were stimulated with $1\times10^5$ autologous DCs and 1 µg/mL anti-CD3 mAb (BD Biosciences) alone or with various numbers of suppressor cells. The cells were cultured for 3 days in 96-well flat-bottom plates and CFSE dilution was analyzed by FACS.

Example 2

Increased Numbers of CD4$^+$ CD$^{25}$ Foxp3$^+$ Treg Cells are Generated by Blocking C5aR In view of our previous findings that during APC:T cell interactions, increased levels of C5a is locally generated from Daf1$^{-/-}$ APCs, we next examined whether C5aR signaling is integrally involved in FoxP3$^+$ Treg cell generation. We set up another MLR by mixing WT C57BL/6 peritoneal macrophages (H-2$^b$) and WT Balb/C CD4$^+$ T cells (H-2d) as we did before. In different wells, we added 200 nM of a potent peptidomimetic C5aR antagonist JPE-1375, or the same volume of PBS. At day 12, we quantified the CD4$^+$CD25$^+$Foxp3$^+$ Treg cell numbers by flow cytometry. These assays showed that blocking C5aR activity with C5aR antagonist increases FoxP3$^+$ Treg generation by ~2 fold. These results suggest that C5aR signaling either in APCs and/or T cells inhibits Treg cell generation.

Increased Numbers of CD4$^+$CD25$^+$ FoxP3$^+$ GFP Treg Cells are Generated from CD4$^+$FoxP3$^+$ GFP-Cells by Blocking C5a or C3a In the experiments discussed above, it was not possible to distinguish whether C5aR signaling modulates de novo Treg cell differentiation or existing Treg cell expansion because subgroups of CD4+ T cells were not separated. To address this issue, we flow sorted CD4+ Foxp3 GFP-T cells (H-2$^b$) from foxp3 GFP knockin mice (kindly provided by Dr. VK Krochroo, Harvard University) and mixed them with WT Balb/C peritoneal macrophages (H-2$^d$) to set up a MLR. To block C3a or C5a activity, we added neutralizing anti mouse C3a or C5a mAbs or isotye IgGs in each well. 7 days later, we quantified the CD4+CD25+FoxP3+ Treg cell numbers by flow cytometry. Blocking C3a or C5a during cognate APC:T cell interactions increases Foxp3GFP+ Treg generation about 2 fold from the foxp3 GFP-precursors. These results indicate that locally generated C5a and C3a inhibits Treg cell differentiation from naive CD4+foxp3-precursors.

Increased Numbers of CD4+ CD25+ Treg Cells are Expanded by C3aR$^{-/-}$C5aR$^{-/-}$ APCs To examine whether C3aR/C5aR signaling in APCs regulates the expansion of existing Treg cells, we next flow sorted CD4+CD25+ Treg cells from Balb/C mice (H-2$^d$) and mixed them with WT or C5aR$^{-/-}$C3aR$^{-/-}$ bone marrow-derived dendritic cells (BM-DCs) (H-2$^b$) together with 1000 U/ml IL-2 to set up a MLR. After 3 days of incubation, we counted total live cell numbers by trypan blue staining and assessed the percentages of CD4+CD25+FoxP3+ Treg cells in the populations. These assays showed that C3aR$^{-/-}$C5aR$^{-/-}$ DCs expanded ~two fold larger numbers of the sorted Treg cells than WT DCs, suggesting that C3aR/C5aR signaling in APCs inhibits the expansion of existing Treg cells.

IL-6 Productions is Reduced in C3aR$^{-/-}$C5aR$^{-/-}$ Dendritic Cells

The above two experiments using sorted CD4+Foxp3$^-$ precursors and CD4+CD25$^-$ Treg cells indicate that C3aR/C5aR signaling inhibits both Treg cell differentiation and expansion. We next measured levels of IL-6 produced by resting WT and C3aR$^{-/-}$C5aR$^{-/-}$ BM-DCs by ELISA. We isolated bone marrow cells from WT and C3aR$^{-/-}$C5aR$^{-/-}$ mice and incubated them with GM-CSF and IL-4 to generate BM-DCs following the standard protocol as described before. We collected culture supernatants at day 6 for IL-6 ELISA. These assays showed that C3aR$^{-/-}$C5aR$^{-/-}$ BM-DCs produce about 3 fold less amounts of IL-6 than WT BM-DCs. These data, together with previous reports on the critical role of IL-6 in Treg cell differentiation and maintenance, suggest that IL-6 could be mechanistically linked to the above observations in which C3aR/C5aR signaling in APCs inhibits Treg cell differentiation/expansion. Increased numbers of CD4+CD25+Foxp3+ Treg cells are generated from CD4+ CD25$^-$ T cells deficient of C3aR and C5aR.

The above experiments address potential impacts of C3aR/C5aR signaling in APCs on Treg cell differentiation/expansion. As indicated above, since both APCs and T cells express C3aR and C5aR, both types of cells could be modulated by the locally generated C3a and C5a. We next tested whether the absence of C3aR/C5aR signaling in T cells favors FoxP3+ Treg cell generation. We isolated CD4+ CD25$^-$ T cells from WT and CaR$^{-/-}$C5aR$^{-/-}$ mice by flow sorting and incubated them with plate-bound anti CD3 mAb (5 µg/ml) together with 25 ng/ml TGF-β. We assessed numbers of CD4+CD25+Foxp3+ Treg cells 3 days later and the assays showed that the generation of CD4+CD25+ Foxp3+ Treg cells from C3aR and C5aR deficient CD4+ CD25$^-$ T cells was more than 2 fold larger than that from the WT T precursors (39.4% vs. 14.9%). These results indicate that in addition to its effects on APCs, C3aR/C5aR signaling in T cells directly inhibits Treg cell generation from their CD4+CD25$^-$ precursors.

Increased Numbers of CD4+CD25+FoxP3+ Treg Cells are Expanded from Existing CD4+CD25+ Treg Cells Deficient of C3aR and C5aR To study whether C3aR/C5aR signaling in T cells will have direct impact on the expansion of existing Treg cells, we flow sorted CD4+CD25+ Treg cells from WT and C5aR3 C3a$^{-/-}$ mice, then activated them with plate coated anti CD3 mAb as described above together with 2000 U/ml IL-2. After 3 days of culture, we counted total live cell numbers by trypan blue staining and assessed CD4+CD25+FoxP3+ Treg cell percentages by flow cytometry. These assays showed that there were 3.5×10$^5$ total FoxP3+ Treg cells expanded from 1×10$^5$ WT Treg cells and 6.3×10$^5$ FoxP3+ Treg cells expanded from the same numbers of C3aR$^{-/-}$ C5aR$^{-/-}$ Treg cells. These results indicate that C3aR/C5aR signaling in T cells directly suppresses existing Treg cell expansion.

CTLA-4 Levels are Increased in C3a$^{-/-}$C5a$^{-/-}$ Treg Cells

As described (Background), previous studies indicated that CTLA-4 is critical for Treg cell function. To investigate the mechanism underlying increased suppressive activity of C3aR$^{-/-}$C5aR$^{-/-}$ Treg cells in the above experiments, we next flow sorted WT and C3aR$^{-/-}$C5aR$^{-/-}$ Treg cells then compared total CTLA-4 levels between them by staining both the cell surface and intracellular CTLA-4 with a PE conjugated anti CTLA-4 mAb (BD Biosciences, Calif.). Because previous studies showed that Treg cells exhibit significantly augmented suppressive activity after activation, we stimulated the WT and C5aR$^{-/-}$C3aR$^{-/-}$ Treg cells by anti CD3/CD28 beads plus 1000 U/ml of IL-2 for 18 hr, then assessed the CTLA-4 levels again. These assays showed that at resting states, C5aR$^{-/-}$C3aR$^{-/-}$ Treg cells express slightly higher levels of total CTLA-4 than WT Treg cells (MFI 6125 v.s. 6809). After activation, both types of Treg cells markedly upregulate their CTLA-4 expression (~10 fold), while C5aR$^{-/-}$C3aR$^{-/-}$ Treg cells have significantly higher levels of total CTLA-4 than WT Treg cells (MFI 79660 v. 58004), suggesting that C3aR/C5aR signaling in Treg cells could inhibit their CTLA-4 expression thereby suppressing their immunoregulatory function.

cAMP Levels are Augmented in C3aR$^{-/-}$C5aR$^{-/-}$ CD4+ T Cells and Reduced in WT CD4+ T Cells Treated with C3a/C5a Previous work by others has shown that cAMP induces CTLA-4 expression in CD4+ T cells. The underlying mechanism could be that cAMP binds to and activates protein kinase A (PKA), which in turn phosphorylates downstream transcription factor cAMP response element binding protein (CREB) that binds to the cAMP-responsive element (CRE) in the CTLA-4 promoter region and therefore enhancing CTLA-4 transcription. We have analyzed the promoter region (–1302 bp) of mouse CTLA-4 gene using the software package Genomatix (www.genomatix.de) and found that there are three CRE sites in the CTLA-4 promoter region In view of these results, to explore the mechanism underlying increased levels of CTLA-4 in C3aR$^{-/-}$C5aR$^{-/-}$ Treg cells, we compared cAMP levels between flow sorted WT and C3aR$^{-/-}$C5aR$^{-/-}$ Treg cells using a cAMP-GLO kit (Promega, Mich.) after stimulation by forskolin, an adenylyl cyclase activator. These assays showed that C3aR$^{-/-}$ C5aR$^{-/-}$ Treg cells possess higher levels of cAMP than WT Treg cells, suggesting that C3aR/C5aR signal in Treg cells might inhibit cAMP production thereby suppressing CTLA-4 expression.

While this application has been particularly shown and described with references to preferred embodiments thereof, it will be understood by those skilled in the art that various changes in form and details may be made therein without departing from the scope of the application encompassed by the appended claims. All patents, publications and references cited in the foregoing specification are herein incorporated by reference in their entirety.

Having described the invention, the following is claimed:

1. A method of treating inflammation in a subject, the method comprising:
   culturing a naive CD4$^+$ T cell in the presence of antigen presenting cells, anti-CD3, and IL-2;
   administering a C3a antagonist or a C3aR antagonist and a C5a antagonist or a C5aR antagonist to the naive CD4$^+$ T cell at an amount effective to substantially inhibit interaction of C3a and C5a with C3aR and C5aR of the CD4$^+$ T cell, induce TGF-β1 expression of the CD4$^+$ T cell, and induce differentiation of the naive CD4$^+$ T cell into a CD4$^+$FoxP3$^+$ Treg cell; and
   administering a therapeutically effective amount of the CD4$^+$FoxP3$^+$ Treg cells to the subject.

2. The method of claim 1, the C3a antagonist or C3aR antagonist and the C5a antagonist or C5aR antagonist being selected from the group consisting of a small molecule, a polypeptide, and a polynucleotide.

3. The method of claim 2, the polypeptide comprising an antibody directed against at least one of C3a, C5a, C3aR, or C5aR.

4. The method of claim 1, the step of administering the C3a antagonist or the C3aR antagonist and the C5a antagonist or the C5aR antagonist includes administering to the naive CD4$^+$ T cell a C3aR antagonist and an a C5aR antagonist.

5. The method of claim 1, the step of administering the C3a antagonist or the C3aR antagonist and the C5a antagonist or the C5aR antagonist includes administering to the cell a C3a antagonist and a C5a antagonist.

6. The method of claim 1, the CD4$^+$FoxP3$^+$ Treg cells being administered systemically to the subject being treated.

7. The method of claim 1, wherein the C3a antagonist or C3aR antagonist and the C5a antagonist or C5aR antagonist substantially induces naive CD4$^+$ cell expression of CD25, CTLA-4, FoxP3, DAF and C5L2, downregulates dendritic cell B7/CD40 and CD4$^+$ effector cell CD28/CD40 ligand costimulatory molecule expression, and inhibits dendritic cell C5a/C3a production and CD4$^+$ cell C5aR/C3aR signal transduction.

8. The method of claim 1, further comprising the step of isolating the naive CD4$^+$ Tcells from a mammalian subject.

9. The method of claim 1, wherein the antigen presenting cells are dendritic cells.

* * * * *